(12) United States Patent
Cheng et al.

(10) Patent No.: US 11,589,901 B2
(45) Date of Patent: Feb. 28, 2023

(54) EXTERNAL ADJUSTMENT DEVICE

(71) Applicant: NuVasive Specialized Orthopedics, Inc., San Diego, CA (US)

(72) Inventors: Shanbao Cheng, San Diego, CA (US); Everett Van Zuiden, San Diego, CA (US); Luke Bilger, San Diego, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 430 days.

(21) Appl. No.: 16/784,211

(22) Filed: Feb. 6, 2020

(65) Prior Publication Data
US 2020/0253643 A1   Aug. 13, 2020

Related U.S. Application Data

(60) Provisional application No. 62/802,961, filed on Feb. 8, 2019.

(51) Int. Cl.
*A61B 17/70* (2006.01)
*A61B 17/72* (2006.01)
(Continued)

(52) U.S. Cl.
CPC ........ *A61B 17/7011* (2013.01); *H01F 7/0242* (2013.01); *A61B 2017/00876* (2013.01); *A61B 2017/681* (2013.01); *A61B 2560/0204* (2013.01)

(58) Field of Classification Search
CPC ............ A61B 17/7016; A61B 17/7026; A61B 17/7014; A61B 17/7225; A61B 17/66;
(Continued)

(56) References Cited

U.S. PATENT DOCUMENTS

| 2,702,031 A | 2/1955 | Wenger |
| 3,111,945 A | 11/1963 | Von Solbrig |

(Continued)

FOREIGN PATENT DOCUMENTS

| CN | 1697630 A | 11/2005 |
| CN | 101040807 A | 9/2007 |

(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — Jan Christopher L Merene
*Assistant Examiner* — Anna V. Little
(74) *Attorney, Agent, or Firm* — Hoffman Warnick LLC

(57) ABSTRACT

An external adjustment device for non-invasively adjusting an implant, the external adjustment device including a controller in communication with an actuator associated with the adjustable implant and a sensor configured to receive information from or about the adjustable implant. The external adjustment device may further comprise a power source and a display. According to one exemplary embodiment, the external adjustment device comprises a magnetic element configured to generate a rotating magnetic field; and a driver configured to drive the magnetic element to generate the rotating magnetic field and configured to rotate a permanent magnet of an adjustable implant, wherein upon placing the external adjustment device in proximity to an adjustable implant having a permanent magnet the magnetic element is configured to magnetically couple with the permanent magnet, and wherein the external adjustment device is configured to non-invasively determine one or more of a magnetic coupling state and a stalled state of the (Continued)

magnetic element and the permanent magnet disposed within the adjustable implant.

18 Claims, 20 Drawing Sheets

(51) Int. Cl.
*H01F 7/02* (2006.01)
*A61B 17/00* (2006.01)
*A61B 17/68* (2006.01)

(58) Field of Classification Search
CPC . A61B 17/663; A61B 17/666; A61B 17/7011; A61B 2017/00876; A61B 2017/681; A61B 2560/0204; H01F 7/0242
See application file for complete search history.

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,170,488 B1 | 1/2001 | Spillman, Jr. et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |

(56) References Cited

U.S. PATENT DOCUMENTS

| | | |
|---|---|---|
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,082,041 B1 | 12/2011 | Radziemski |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,388,553 B2 | 3/2013 | James et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |

(56) References Cited

U.S. PATENT DOCUMENTS

| | | |
|---|---|---|
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,721,643 B2 | 5/2014 | Morgan et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,915,866 B2 | 12/2014 | Nycz |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,974,366 B1 | 3/2015 | Radziemski et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 10,252,066 B2 | 4/2019 | Radziemski et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0238992 A1 | 10/2007 | Donofrio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0046037 A1 | 2/2008 | Haubrich et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0228231 A1 | 9/2008 | Raphael et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |

(56) References Cited

U.S. PATENT DOCUMENTS

| | | |
|---|---|---|
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1* | 4/2009 | Pool .................. A61B 17/8004 600/587 |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1* | 8/2009 | Phillips .................... A61N 2/12 600/9 |
| 2009/0216113 A1 | 8/2009 | Meier et al. |
| 2009/0270949 A1 | 10/2009 | Kalpin et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060336 A1 | 3/2011 | Pool et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0157889 A1 | 6/2012 | Tanis et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0178915 A1 | 7/2013 | Radziemski et al. |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0336474 A1 | 11/2014 | Arbabian et al. |
| 2014/0343350 A1 | 11/2014 | Martinson et al. |
| 2014/0358150 A1 | 12/2014 | Kaufman et al. |
| 2015/0080639 A1 | 3/2015 | Radziemski et al. |
| 2015/0105782 A1 | 4/2015 | D'Lima et al. |
| 2015/0105824 A1 | 4/2015 | Moskowitz et al. |
| 2015/0257799 A1 | 9/2015 | Janna et al. |
| 2015/0272471 A1* | 10/2015 | Quick ....................... H01F 7/20 600/424 |
| 2015/0335285 A1 | 11/2015 | Poon et al. |
| 2016/0242679 A1* | 8/2016 | Pathak ................. A61B 5/0004 |
| 2017/0125892 A1 | 5/2017 | Arbabian et al. |
| 2017/0319858 A1 | 11/2017 | Radziemski et al. |
| 2017/0333080 A1* | 11/2017 | Roschak ................. A61B 17/68 |
| 2018/0271452 A1* | 9/2018 | Bonnet ................... G06F 1/329 |

FOREIGN PATENT DOCUMENTS

| | | | | |
|---|---|---|---|---|
| CN | 113412090 A | 9/2021 | | |
| DE | 1541262 A1 | 6/1969 | | |
| DE | 8515687 U1 | 12/1985 | | |
| DE | 19626230 A1 | 1/1998 | | |
| DE | 19745654 A1 | 4/1999 | | |
| DE | 102005045070 A1 | 4/2007 | | |
| EP | 0663184 A1 | 7/1995 | | |
| EP | 1905388 A1 | 4/2008 | | |
| EP | 2683146 A1 * | 1/2014 | ........ | H04M 1/72527 |
| EP | 3920808 A1 | 12/2021 | | |
| FR | 2901991 A1 | 12/2007 | | |
| FR | 2900563 B1 | 8/2008 | | |
| FR | 2892617 B1 | 9/2008 | | |
| FR | 2916622 B1 | 9/2009 | | |
| FR | 2961386 B1 | 12/2011 | | |
| JP | H0956736 | 3/1997 | | |
| JP | 2002500063 A | 1/2002 | | |
| JP | 2022519731 A | 3/2022 | | |
| WO | WO1998044858 A1 | 10/1998 | | |
| WO | WO1999051160 A1 | 10/1999 | | |
| WO | WO2001024697 A1 | 4/2001 | | |
| WO | WO2001045485 A3 | 6/2001 | | |
| WO | WO2001045487 A2 | 6/2001 | | |
| WO | WO2001067973 A2 | 9/2001 | | |
| WO | WO2001078614 A1 | 10/2001 | | |
| WO | WO2007013059 A3 | 2/2007 | | |
| WO | WO2007015239 A3 | 2/2007 | | |
| WO | WO2011116158 A3 | 9/2011 | | |
| WO | WO2013119528 A1 | 8/2013 | | |
| WO | WO2014040013 A1 | 3/2014 | | |
| WO | WO-2015183225 A1 * | 12/2015 | ......... | A61B 17/6466 |
| WO | 2016065205 A1 | 4/2016 | | |
| WO | WO-2017100774 A1 * | 6/2017 | ......... | A61B 17/7016 |
| WO | 2018152203 A2 | 8/2018 | | |
| WO | WO-2018152203 A2 * | 8/2018 | ......... | A61B 17/3468 |
| WO | 2020163800 A1 | 8/2020 | | |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

(56) References Cited

OTHER PUBLICATIONS

Amer et al., "Evaluation of treatment of late-onset tibia vara using gradual angulation translation high tibial osteotomy", ACTA Orthopaedica Belgica, 2010, pp. 360-366, 76, No. 3.
Angrisani et al., "Lap-Band® Rapid Port™ System: Preliminary results in 21 patients", Obesity Surgery, 2005, p. 936, 15, No. 7.
Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
Invis®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.

(56) References Cited

OTHER PUBLICATIONS

Krieg et al., "Leg lengthening with a motorized nail in adolescents.", Clinical Orthopaedics and Related Research, 2008, pp. 189-197, 466, No. 1.

Kucukkaya et al., "The new intramedullary cable bone transport technique.", Journal of Orthopaedic Trauma, 2009, pp. 531-536, 23, No. 7.

Lechner et al., "In vivo band manometry: A new method in band adjustment", Obesity Surgery, 2005, p. 935, 15, No. 7.

Lechner et al., "Intra-band manometry for band adjustments: The basics", Obesity Surgery, 2006, pp. 417-418, 16, No. 4.

Li et al., "Bone transport over an intramedullary nail: A case report with histologic examination of the regenerated segment.", Injury, 1999, pp. 525-534, 30, No. 8.

Lonner, "Emerging minimally invasive technologies for the management of scoliosis.", Orthopedic Clinics of North America, 2007, pp. 431-440, 38, No. 3.

Matthews et al., "Magnetically adjustable intraocular lens.", Journal of Cataract and Refractive Surgery, 2003, pp. 2211-2216, 29, No. 11.

Micromotion, "Micro Drive Engineering•General catalogue.", 2009, pp. 14-24.

Mineiro et al., "Subcutaneous rodding for progressive spinal curvatures: Early results.", Journal of Pediatric Orthopaedics, 2002, pp. 290-295, 22, No. 3.

Moe et al., "Harrington instrumentation without fusion plus external orthotic support for the treatment of difficult curvature problems in young children.", Clinical Orthopaedics and Related Research, 1984, pp. 35-45, 185.

Montague et al., "Magnetic gear dynamics for servo control.", Melecon 2010—2010 15th IEEE Mediterranean Electrotechnical Conference, Valletta, 2010, pp. 1192-1197.

Montague et al., "Servo control of magnetic gears.", IEEE/ASME Transactions on Mechatronics, 2012, pp. 269-278, 17, No. 2.

Nachemson et al., "Intravital wireless telemetry of axial forces in Harrington distraction rods in patients with idiopathic scoliosis.", The Journal of Bone and Joint Surgery, 1971, pp. 445-465, 53, No. 3.

Nachlas et al., "The cure of experimental scoliosis by directed growth control.", The Journal of Bone and Joint Surgery, 1951, pp. 24-34, 33-A, No. 1.

Newton et al., "Fusionless scoliosis correction by anterolateral tethering . . . can it work?.", 39th Annual Scoliosis Research Society Meeting, 2004.

Oh et al., "Bone transport over an intramedullary nail for reconstruction of long bone defects in tibia.", Archives of Orthopaedic and Trauma Surgery, 2008, pp. 801-808, 128, No. 8.

Ozcivici et al., "Mechanical signals as anabolic agents in bone.", Nature Reviews Rheumatology, 2010, pp. 50-59, 6, No. 1.

Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.

Prontes, "Longest bone in body.", eHow.com, 2012.

Rathjen et al., "Clinical and radiographic results after implant removal in idiopathic scoliosis.", Spine, 2007, pp. 2184-2188, 32, No. 20.

Ren et al., "Laparoscopic adjustable gastric banding: Surgical technique", Journal of Laparoendoscopic & Advanced Surgical Techniques, 2003, pp. 257-263, 13, No. 4.

Reyes-Sanchez et al., "External fixation for dynamic correction of severe scoliosis", The Spine Journal, 2005, pp. 418-426, 5, No. 4.

Rinsky et al., "Segmental instrumentation without fusion in children with progressive scoliosis.", Journal of Pediatric Orthopedics, 1985, pp. 687-690, 5, No. 6.

Rode et al., "A simple way to adjust bands under radiologic control", Obesity Surgery, 2006, p. 418, 16, No. 4.

Schmerling et al., "Using the shape recovery of nitinol in the Harrington rod treatment of scoliosis.", Journal of Biomedical Materials Research, 1976, pp. 879-892, 10, No. 6.

Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.

Sharke, "The machinery of life", Mechanical Engineering Magazine, Feb. 2004, Printed from Internet site Oct. 24, 2007 http://www.memagazine.org/contents/current/features/moflife/moflife.html.

Shiha et al., "Ilizarov gradual correction of genu varum deformity in adults.", Acta Orthop Belg, 2009, pp. 784-791, 75, No. 6.

Simpson et al., "Femoral lengthening with the intramedullary skeletal kinetic distractor.", Journal of Bone and Joint Surgery, 2009, pp. 955-961, 91-B, No. 7.

Smith, "The use of growth-sparing instrumentation in pediatric spinal deformity.", Orthopedic Clinics of North America, 2007, pp. 547-552, 38, No. 4.

Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).

Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).

Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

Sun et al., "Masticatory mechanics of a mandibular distraction osteogenesis site: Interfragmentary micromovement.", Bone, 2007, pp. 188-196, 41, No. 2.

Synthes Spine, "VEPTR II. Vertical Expandable Prosthetic Titanium Rib II: Technique Guide.", 2008, 40 pgs.

Synthes Spine, "VEPTR Vertical Expandable Prosthetic Titanium Rib, Patient Guide.", 2005, 26 pgs.

Takaso et al., "New remote-controlled growing-rod spinal instrumentation possibly applicable for scoliosis in young children.", Journal of Orthopaedic Science, 1998, pp. 336-340, 3, No. 6.

Teli et al., "Measurement of forces generated during distraction of growing rods.", Journal of Children's Orthopaedics, 2007, pp. 257-258, 1, No. 4.

Tello, "Harrington instrumentation without arthrodesis and consecutive distraction program for young children with severe spinal deformities: Experience and technical details.", The Orthopedic Clinics of North America, 1994, pp. 333-351, 25, No. 2.

Thaller et al., "Limb lengthening with fully implantable magnetically actuated mechanical nails (PHENIX®)—Preliminary results.", Injury, 2014 (E-published Oct. 28, 2013), pp. S60-S65, 45.

Thompson et al., "Early onset scoliosis: Future directions", 2007, J Bone Joint Surg Am, pp. 163-166, 89-A, Suppl 1.

Thompson et al., "Growing rod techniques in early-onset scoliosis", Journal of Pediatric Orthopedics, 2007, pp. 354-361, 27, No. 3.

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

(56) References Cited

OTHER PUBLICATIONS

Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

* cited by examiner

EXTERNAL ADJUSTMENT DEVICE

RELATED APPLICATIONS

Any and all applications for which a foreign or domestic priority claim is identified in the Application Data Sheet as filed with the present application are hereby incorporated by reference under 37 CFR 1.57.

FIELD OF DISCLOSURE

The present disclosure generally relates to the field of medical devices, and more specifically to external adjustment devices for adjusting adjustable implants.

BACKGROUND

Non-invasively adjustable implants are provided to treat various disorders of the skeletal system. However, feedback from these devices to their external remote controls is limited. Adjustment instructions to adjustable implants are often unidirectional, with the respective remote controls receiving no feedback on the actual adjustments achieved by the adjustable implants. As such, users are often unsure of whether or not the expected adjustment is actually being applied.

SUMMARY

In one exemplary embodiment, an external adjustment device for non-invasively adjusting an implant includes: a magnetic element configured to generate a rotating magnetic field; and a driver configured to drive the magnetic element to generate the rotating magnetic field and configured to rotate a permanent magnet of an adjustable implant.

In another exemplary embodiment, an external adjustment device for non-invasively adjusting an implant, the external adjustment device includes: a controller; a motor; and at least one magnet rotatably coupled to the motor; wherein upon placing the external adjustment device in proximity to an adjustable implant the at least one magnet is configured to magnetically couple with a permanent magnet of the adjustable implant; and wherein the upon a movement of the at least one magnet, the controller is configured to detect a magnetic coupling state of the at least one magnet with the permanent magnet of the adjustable implant.

In another embodiment, an external adjustment device for non-invasively adjusting an implant, the external adjustment device include: a controller; a motor; and at least one magnet rotatably coupled to the motor; wherein upon placing the external adjustment device in proximity to an adjustable implant the at least one magnet is configured to magnetically couple with a permanent magnet of the adjustable implant; and wherein the upon a movement of the at least one magnet, the controller is configured to determine a magnetic coupling state of the at least one magnet with a magnet disposed within the adjustable implant According to one method for adjusting an implant, the method comprising the steps: positioning an external adjustment device in proximity to an adjustable implant; coupling at least one magnet of the external adjustment device with a permanent magnet of the adjustable implant; generating a changing magnetic field by rotating the at least one magnet of the external adjustment device; monitoring a rotation speed of the at least one magnet of the external adjustment device to determine a magnetic coupling state of the at least one magnet with the permanent magnet of the adjustable implant.

According to an exemplary embodiment, a method for obtaining a characterization profile of an external adjustment device includes the steps: rotating a magnet of the external adjustment device; measuring an acceleration array during a revolution of the magnet; determining an acceleration peak of the acceleration array; shifting the acceleration array to a center peak; averaging all measured acceleration arrays; saving averaged array as a characterization profile of the external adjustment device.

In an exemplary embodiment, a method for determining a coupled state of a magnet of an external adjustment device with a permanent magnet of an adjustable implant includes the steps: rotating a magnet of the external adjustment device; measuring an acceleration array during a revolution of the magnet; determining an acceleration peak of the acceleration array; shifting the acceleration array to a center peak; averaging all measured acceleration arrays; subtracting an averaged array from a characterization profile of the external adjustment device to obtain a test array; and comparing peak to peak amplitude of the test array to a threshold, wherein if peak to peak amplitude of the test array is greater than the threshold, then a coupled state is determined; and wherein if peak to peak amplitude of the test array is less than the threshold, then an uncoupled state is determined.

In an exemplary embodiment, a method for determining a stalled state of a permanent magnet of an adjustable implant using an external adjustment device includes the steps: rotating a magnet of the external adjustment device; measuring an acceleration array during a revolution of the magnet; determining an acceleration peak of the acceleration array; shifting the acceleration array to a center peak; averaging all measured acceleration arrays; subtracting averaged array from a characterization profile of the external adjustment device to obtain a test array; performing a fast Fourier transform (FFT) analysis of the test array; and observing a 3rd harmonic of the FFT, wherein if a 3rd harmonic is one or more of: present and above a threshold value, then a stalled state is determined, and wherein if a 3rd harmonic is one or more of: missing and below a threshold value, then no stalled state is detected and the magnets are coupled.

BRIEF DESCRIPTION OF THE DRAWINGS

These and other features will be further understood by those with skill in the art upon a review of the appended drawings, wherein.

DETAILED DESCRIPTION

Figure 1:
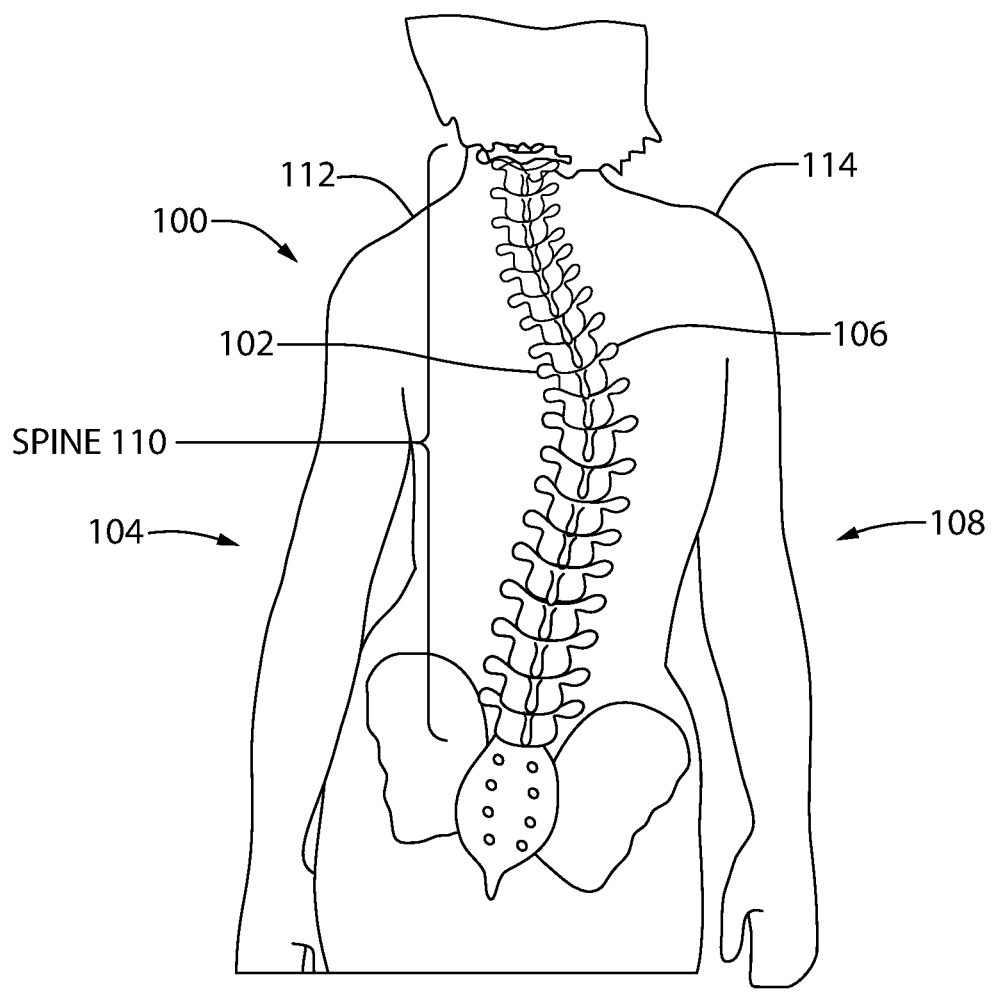
FIG. 1 shows a spine of a person with scoliosis.

For purposes of explanation and not limitation, details and descriptions of certain preferred embodiments are hereinafter provided such that one having ordinary skill in the art may be enabled to make and use the invention. These details and descriptions are representative only of certain preferred embodiments, however, and a myriad of other embodiments which will not be expressly described will be readily understood by those having skill in the art upon a thorough review hereof. Accordingly, any reviewer of the instant disclosure should interpret the scope of the invention by the claims, and such scope shall not be limited by the embodiments described and illustrated herein.

In a general embodiment, an external adjustment device is in communication with an adjustable implant. The external adjustment device may include a controller in communication with an actuator associated with the adjustable implant. The external adjustment device may also include at least one sensor configured to receive information from or about the adjustable implant. The external adjustment further includes a power source. According to one aspect, the external adjustment device may include a display. According to another aspect, the controller may be removable from the external adjustment device.

In some embodiments, the external adjustment device may include a magnetic element configured to generate a rotating magnetic field, and a driver configured to drive the magnetic element to generate the rotating magnetic field and configured to rotate a permanent magnet of an adjustable implant.

In some embodiments, the magnetic element may include a magnet and the driver may include an actuator configured to rotate the magnet and configured to generate the rotating magnetic field.

In some embodiments, the magnetic element includes a rotatable magnet. The magnetic element may include a hollow rotatable magnet having a tapered profile secured to a magnet drive shaft having a tapered profile. The hollow rotatable magnet may be secured to the magnet drive shaft by a cap.

The driver may include a motor configured to rotate the magnetic element to generate the rotating magnetic field. For example, the motor may be an electric motor.

The controller may be configured to be removably attached to a housing of the external adjustment device. The controller may include handheld electronic device. For example, the controller may be a smartphone.

The external adjustment device may include a power storage device. For example, one or more of a rechargeable battery and a capacitor. of claim 1, further comprising a rotational speed sensor configured to monitor one or more of a rotational speed of the driver and a rotational speed of the magnetic element.

In some embodiments, the controller may be configured to determine one or more of: a magnetic coupling state and a stall state of the permanent magnet of the adjustable implant. The determination may include transforming an acceleration array using a fast Fourier transform (FFT) and observing a third harmonic of the fast Fourier transform (FFT).

In addition to common definitions as readily understood by those having skill in the art, as used herein, fast Fourier transform (FFT) may be considered an algorithm that computes the discrete Fourier transform (DFT) of a sequence, or its inverse (IDFT). Fourier analysis converts a signal from its original domain (often time or space) to a representation in the frequency domain and vice versa.

FIG. 1 shows an illustration of a patient 100 with scoliosis. The patient 100 may include a human being or any mammalian animal. The concave portion 102 of the spinal curve can be seen on the left side 104 of the patient 100, and the convex portion 106 can be seen on the right side 108 of the patient 100. In some patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
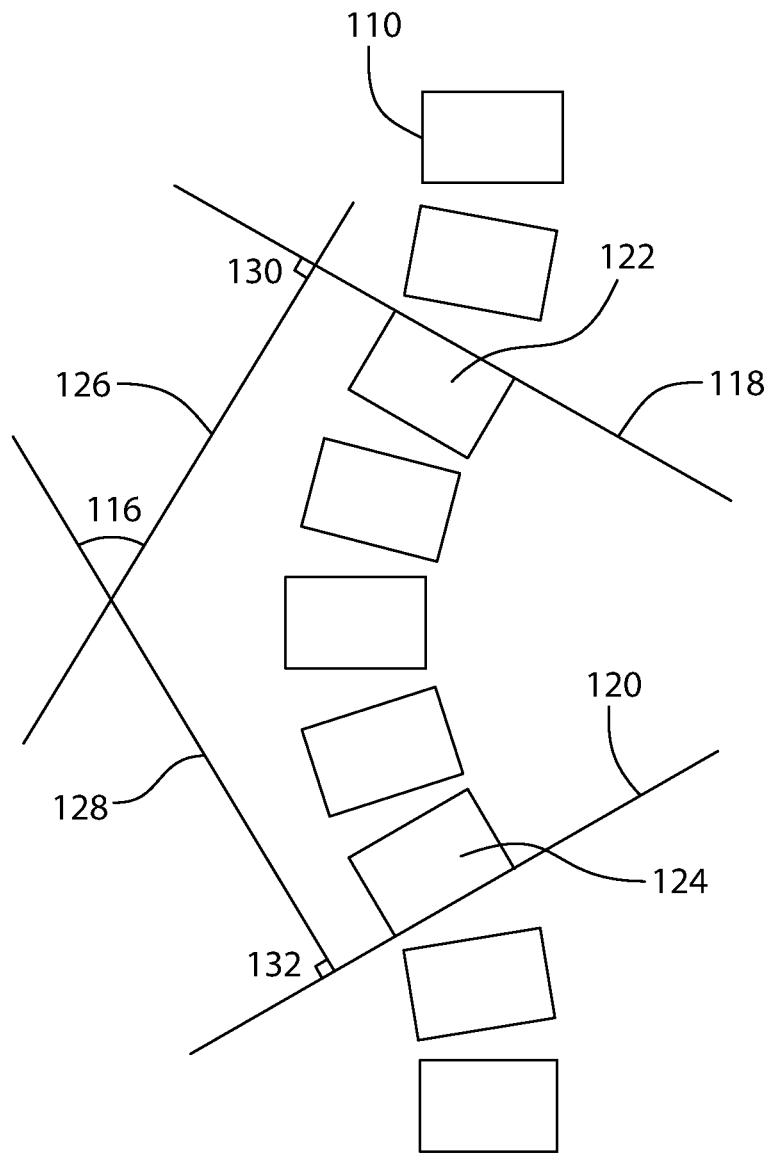
FIG. 2 shows a cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
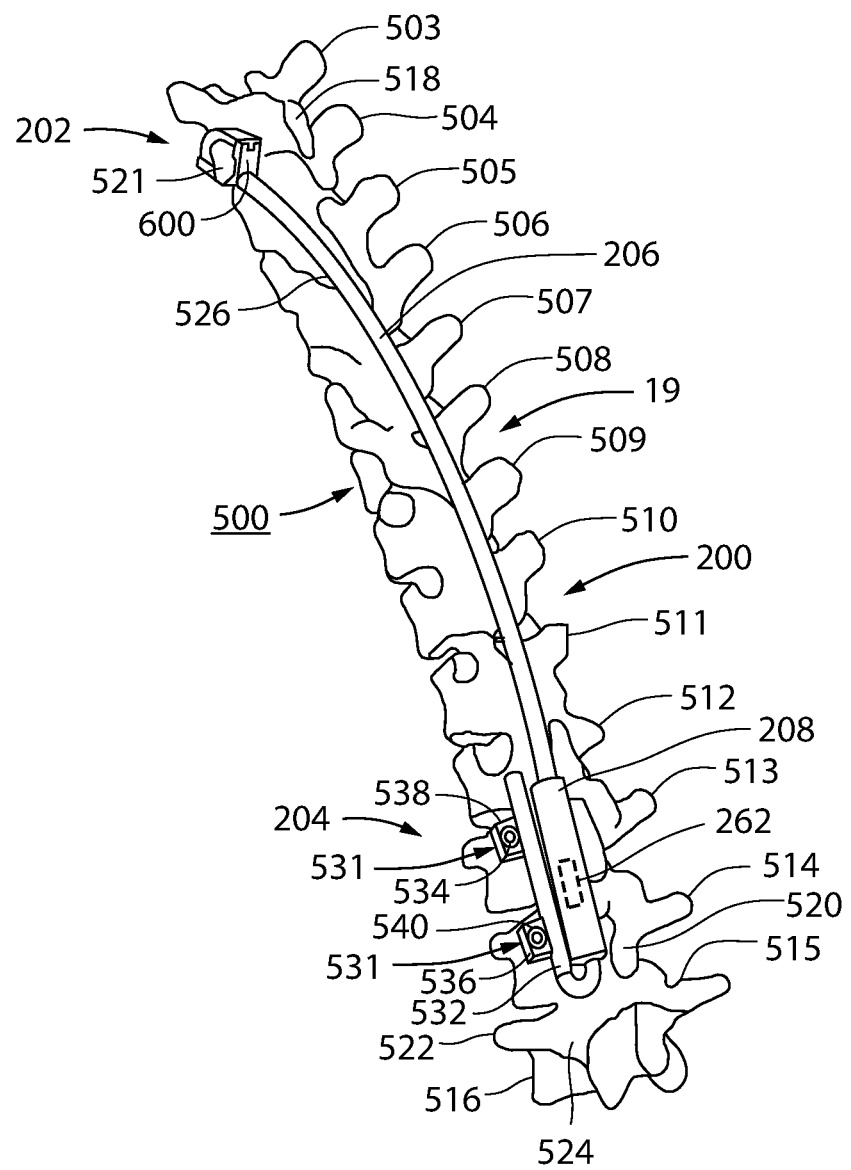
FIG. 3 shows a first exemplary adjustable implant having a permanent magnet mounted on the spine of a patient.

FIG. 3 illustrates an adjustable implant 200 for treating scoliosis according to one embodiment. The adjustable implant 200, is fixated at its upper end 202 and lower end 204 to the patient's spine 500. The illustrated example of the spine 500 includes the particular thoracic and lumbar vertebrae that typically encompass a scoliotic curve, for example the curve of a patient with adolescent idiopathic scoliosis. The T3 through T12 thoracic vertebrae, 503, 504, 505, 506, 507, 508, 509, 510, 511, 512, respectively and the L1 through L3 vertebrae, 513, 514, 515 are depicted in FIG. 3, not in a severe scoliotic condition, but in a very slight residual curve that represents a modest curve that has been partially or completely straightened during the implantation procedure.

Each vertebra is different from the other vertebra by its size and shape, with the upper vertebra generally being smaller than the lower vertebra. However, generally, the vertebrae have a similar structure and include a vertebral body 516, a spinous process 518, 520, laminae 526, transverse processes 521, 522 and pedicles 524.

In this embodiment, the adjustable implant 200 includes a distraction rod 206 which is adjustable (lengthwise) via a coupled adjustable portion 208. The distraction device is fixated to the spine 500 via a clamp 600 at the upper end 202 of the distraction rod 206. In FIG. 3, the clamp 600 is secured around the transverse process 521 of the T4 vertebra 504. Alternatively, the clamp 600 may be secured around an adjacent rib (not shown) or rib facet. In still another alternative, the clamp may be replaced by a laminar and pedicle hook system, or pedicle screw system. Exemplary pedicle hook systems or pedicle screw systems may be found in U.S. patent application Ser. Nos. 12/121,355 and 12/250,442 which are incorporated by reference as if set forth fully herein.

Referring back to FIG. 3, the adjustable implant 200 is illustrated as being fixated to the spine 500 with a pedicle screw system 531 comprising a connecting rod 532 and two toe clamps 538, 540. The connecting rod 532 then interfaces with the adjustable portion 208. The adjustable portion 208 of the adjustable implant 200 contains a magnetic assembly 210 (illustrated in dashed lines) having a permanent magnet 262 configured to drive a lead screw that, depending on the direction of rotation of the internal magnet, will extend or retract the distraction rod 206 using the adjustable portion 208. Lengthening of the distraction rod 206, for example, will impart a distraction force to the spine 500. Retracting the distraction rod 206 will lower or remove the distraction force on the spine 500, for example if too high a distraction force causes pain or complications. It may even be desired to use the device to compress the spine or bone, for example at an anterior portion of the spine or at the convex portion of a curve. In some embodiments the adjustable implant may comprise a distraction device. Examples of various magnetic assemblies 210 for use in distraction devices may be found in U.S. patent application Ser. Nos. 12/121,355 and 12/250,442.

Still referring to FIG. 3, a locking screw 534 can be loosened to adjust the angle of the connecting rod 532 into the desired orientation and then locking screw 534 can be tightened so that toe clamp 538 securely holds connecting rod 532 in place without further rotation. The second toe clamp 540 is adjusted in the same way, by tightening locking screw 536. Because a scoliotic spine is also rotated (usually the center section is rotated to the right in AIS patients), the non-fusion embodiment presented here allows de-rotation of the spine 500 to happen naturally, because there is no fixation at the middle portion of the adjustable implant 200.

In order to further facilitate this de-rotation, the adjustable implant 200 may allow for free rotation at its ends. For example, the adjustable portion 208 may be coupled to the connecting rod 532 via an articulating joint. U.S. patent application Ser. Nos. 12/121,355 and 12/250,442 describe various articulating interfaces and joints that may be utilized to couple the adjustable portion 108 to the connecting rod 532 or the like.

It should be noted that distraction rod 206 may be precurved with the typical shape of a normal saggital spine, but it should also be noted that the curve may be slightly different than standard scoliosis fusion instrumentation, because in the non-fusion embodiment described herein, the adjustable implant 200 is not flush with the spine but rather is placed either subcutaneous or subfascial, and thus is not below the back muscles. The only portions of the adjustable implant 200 that are designed to be placed below the muscles are the clamp 600 and the portion of the distraction rod 206 immediately adjacent the clamp 600, the pedicle screw system 531 and the connecting rod 532. Thus, FIG. 3 illustrates an embodiment in which the bulk of the hardware associated with the adjustable implant 200 is placed over the muscle. It should be understood, however, that in alternative configurations, any other part of the entire implantable embodiment may be placed under the muscle (i.e., submuscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection. Further, it may be desirable to produce the "J" curve of the connecting rod 532 or any other curve at the connecting rod 532 with optional flanges or ribs at their highest stress points in order to increase their durability in demanding implant conditions.

Figure 4:
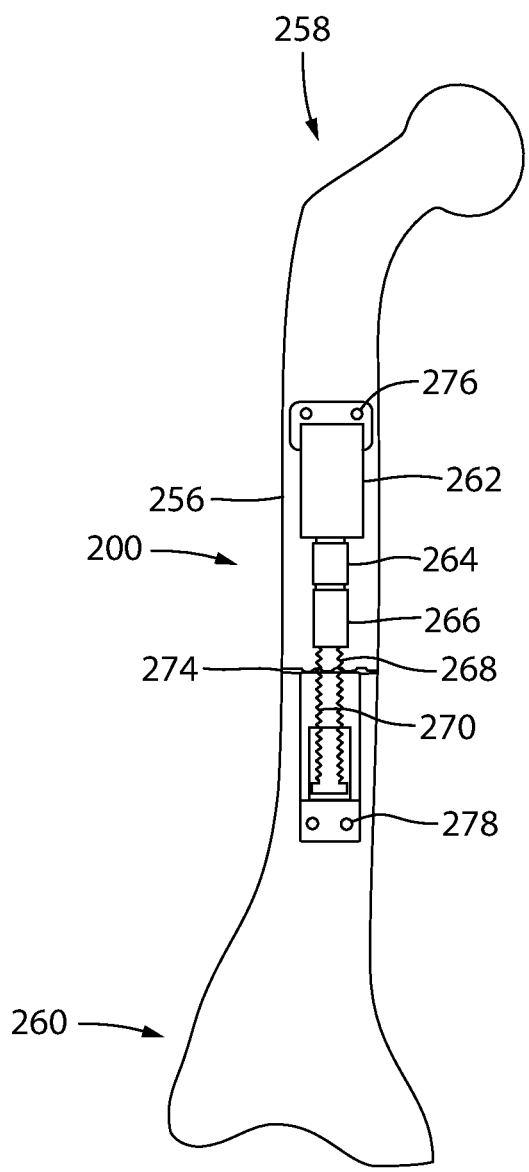
FIG. 4 shows a second exemplary adjustable implant having a permanent magnet mounted in a bone of a patient.

FIG. 4 illustrates an adjustable implant 200 in accordance with an alternative embodiment, that includes a bone growth device that is attached to bone 256 having a proximal portion 258 and a distal portion 260 by a proximal securement, member 276 and a distal securement member 278. The securement members 276, 278 may operate using any number of securement devices or methods known to attach a device to bone, including screws, clamps or even adhesive materials. In cases of a bone fracture, a fracture site 274 is illustrated, though it should be noted that this fracture is not always present in some of the applications. As seen in FIG. 4, the adjustable implant 200 includes a magnetic assembly 210 that includes a permanent magnet 262 that is configured to rotate on its axis in response to an externally applied magnetic field. Rotation of the permanent magnet 262 effectuates rotation of a planetary gear set 266. An optional slip clutch 264 is illustrated as being disposed between the permanent magnet 262 and the planetary gear set 266, though slip clutch 264 may be disposed at any other location along the drive transmission. Rotation of the planetary gear set 266 in a first direction (e.g., clockwise or counter-clockwise depending on configuration) causes lead screw 268 to turn within internal thread 270 causing distraction (e.g., elongation) of the bone 256. Bone growth distraction device 272 may be implanted in a single operation. Subsequent adjustments are performed non-invasively, and if desired can he performed frequently in order to precisely control bone growth. An exemplary daily adjustment in bone distraction is 1 mm. An adjustment device such as external adjustment device 700 described herein may be used to rotate the permanent magnet 262. An external adjustment device 700 of the type described herein may also be used to distract and retract the adjustable implant 200 illustrated in FIG. 3 by magnetic coupling to its magnetic assembly 210. The permanent magnet 262 may include for example a cylindrical magnet.

As one with skill in the art may appreciate, although certain illustrated embodiments of adjustable implants are included herein, it is contemplated and this disclosure is intended to include all known adjustable implants configured to be adjusted by an external adjustment device, including for example, adjustable intramedullary nails.

Figure 5:
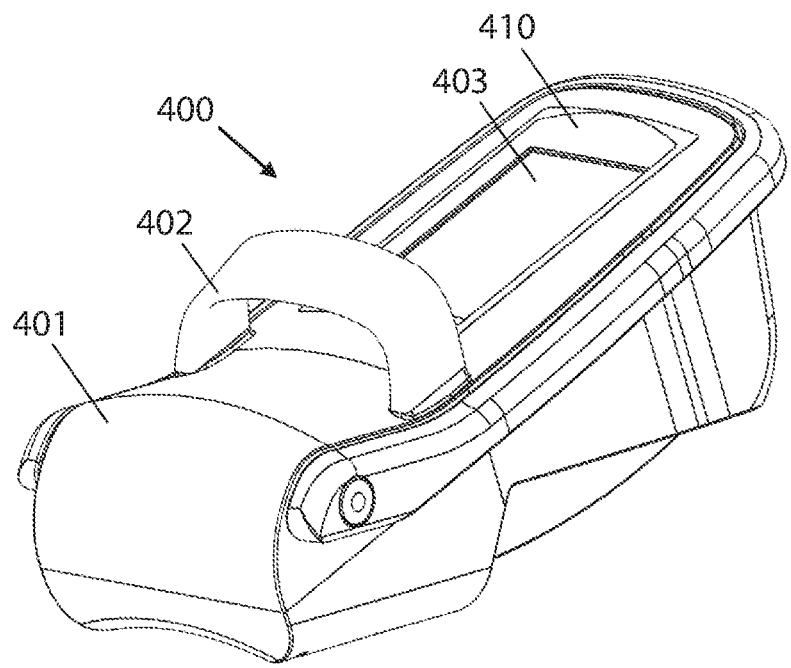
FIG. 5 shows a perspective view of an external adjustment device in accordance with a first embodiment.

FIG. 5 shows a perspective view of an exemplary external adjustment device 400 for adjusting adjustable implants. The external adjustment device 400, may include a housing 401 having a handle 402 and a display 403. In some embodiments, the display 403 may be integrated with the housing 401 of the external adjustment device 400. In the illustrated embodiment, the external adjustment device 400 is configured to receive a removable controller 410 having a display 403, with the display 403 being an integral part of the removable controller 410.

According to an exemplary embodiment, the controller 410 may be a handheld electronic device. The handheld electronic device may be, for example, a smartphone, a tablet, and any other known handheld electronic device. The handheld electronic device may contain and may be operatively connected to a display and/or one or more wireless communication protocols (e.g., Wi-Fi or Bluetooth®). The display of the handheld electronic device may be disposed adjacent to a top surface of the external adjustment device 400, such that the display 403 can communicate information to and receive instructions from a user during use.

For example, in some embodiments the display 403 may present to a user a graphical user interface (GUI). The display 403 may include one or more of a touchscreen or touchscreen technology, including, for example, capacitive touchscreen technology. The GUI may communicate adjustment instructions to a user which may correspond to a treatment regimen to guide the user in adjusting the adjustable implant in accordance with the treatment regimen. Additionally, the GUI may include one or more touchscreen digital buttons configured to activate and control the external adjustment device 400.

Figure 6:
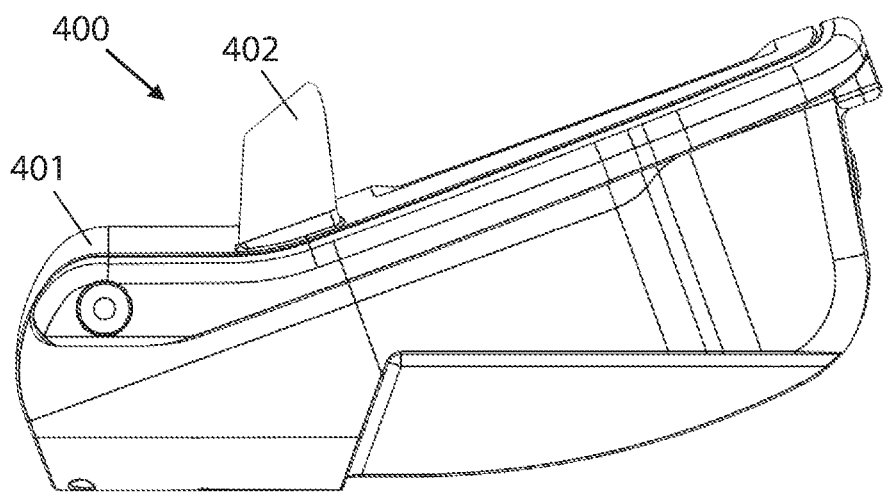
FIG. 6 shows a side view of the external adjustment device in accordance with the first embodiment.
Figure 7:
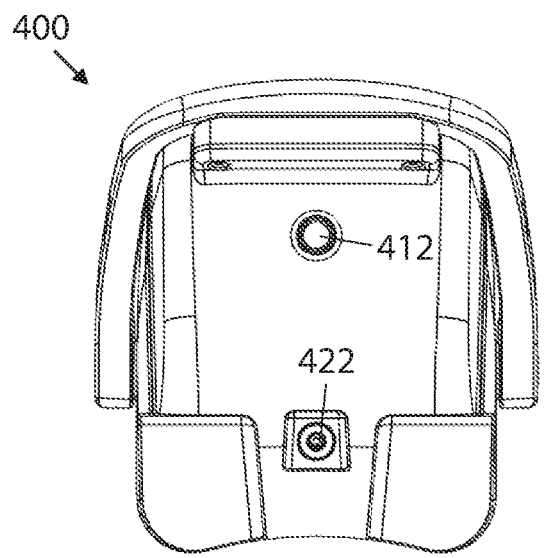
FIG. 7 shows a front view of the external adjustment device in accordance with the first embodiment.

FIG. 6 shows a side view of the external adjustment device 400 in accordance with the first embodiment. The handle 403 shown extending upwardly from the housing 401. FIG. 7 shows a front view of the external adjustment device 400, the external adjustment device 400 including a power supply input 422 and a data connection port 412. Additionally, a bottom surface of the housing 401 is shown including a curvature configured to form to a patient's body and minimize a distance (GAP) between the magnet 440 and a permanent magnet 262 of the adjustable implant. The power supply input 422 may be configured to removably receive an AC power supply. The data connection port 412 may be configured to removably receive a data communication cable. The data communication cable may be configured to connect the external adjustment device 400 to a tertiary device to one or more of update the controller 410 software and download data from the controller 410.

Figure 8:
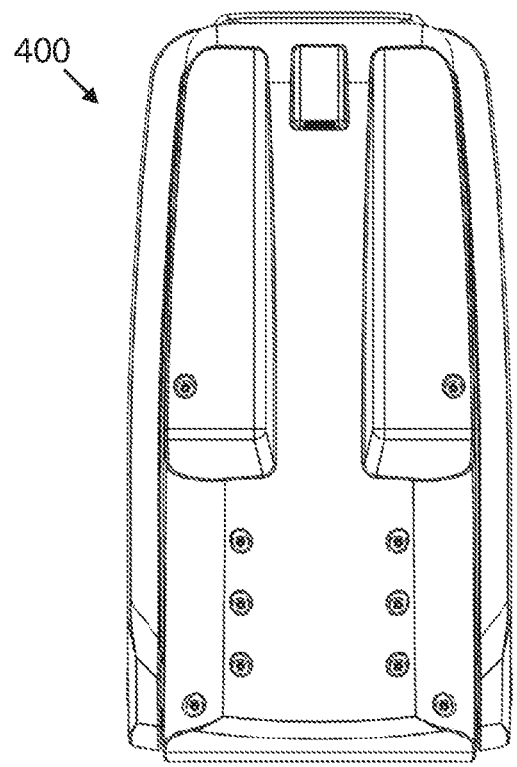
FIG. 8 shows a bottom view of the external adjustment device in accordance with the first embodiment.

FIG. 8 shows a bottom view of the external adjustment device 400, a bottom surface of the housing 401 is shown including a curvature configured to form to a patient's body and minimize a distance (GAP) between the magnet 440 and a permanent magnet 262 of the adjustable implant.

Figure 9:
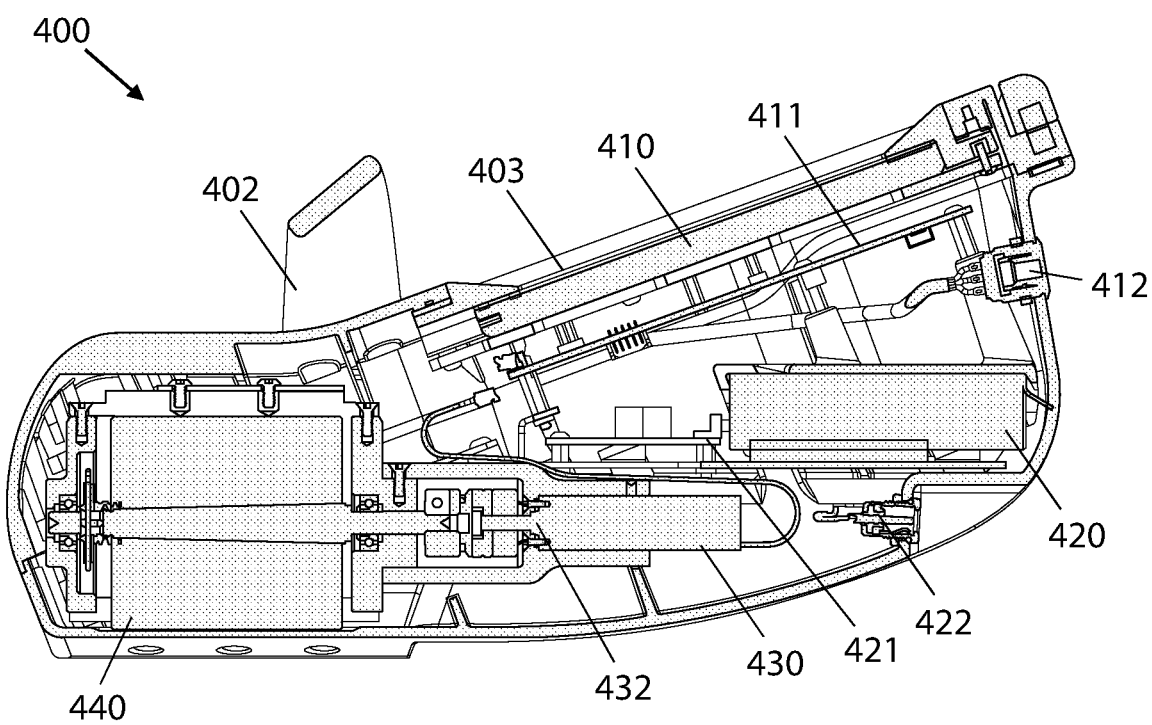
FIG. 9 shows cross-sectional side view the external adjustment device in accordance with the first embodiment.

FIG. 9 shows a cross-sectional side view of the external adjustment device 400 in accordance with the first embodiment. The external adjustment device 400 shown including a housing 401, a controller 410, an internal power storage device 420, a motor 430, and at least one magnet 440.

The internal power storage device 420 and wireless communication capabilities of the controller 440, may provide for wireless operation of the external adjustment device 400. The internal power storage device 420 may negate the need for a power chord during operation. The controller 410 may provide a low voltage control system negating the need for a bulky external control module. And wireless communication capabilities, for example one or more of RF, Wi-Fi Bluetooth® may enable the external adjustment device 400 and the controller 410 for remote operation. The remote operation may be achieved by one or more of a tertiary device in the same room, and across the internet by a tertiary device on the other side of the globe.

In some embodiments, the controller 410 may be a control board disposed within the housing 401 of the external adjustment device 400. The display 403 may include any type of display 403, including for example: LED, LCD, OLED, and any other known display and touchscreen technology. The control interface board 411 may contain or be in communication with one or more communication circuit, for example, one or more of Wi-Fi, cellular networks, or Bluetooth®, enabling communication between the external adjustment device 400 and one or more tertiary devices.

In FIG. 9 the controller 410 is shown operably connected to a controller interface board 411 by at least one interconnect. In some embodiments, this connection may be established via a physical connection as illustrated and in some embodiments a wireless connection, for example, Bluetooth®. The control interface board 411 may be further connected to one or more of a power interface board 421, the power storage device 420, and the actuator 430.

The controller 410 may be remotely accessible and remotely controllable by a tertiary device allowing for remote operation of the external adjustment device 400 by a user from outside of a sterile field.

The external adjustment device 400 is also shown including an internal power storage device 420. The power storage device 420 may include a battery, a capacitor, and any other power storage device known and used in the art. The power storage device may be rechargeable and the external adjustment device 400 may include a recharging circuit configured to recharge the power storage device 420 using an external power source. The external power source, for example a power supply, may be operably connected to the recharging circuit of the power storage device via the power supply input. The power storage device 420, and/or at least a portion of the recharging circuit, may be disposed adjacent to a surface of the external adjustment device 400, enabling connection of a power supply charge cable to the external adjustment device 400. In some embodiments, the recharging circuit may enable wireless charging of the internal power storage device 420, using induction to wirelessly transfer power. In some embodiments, the recharging circuit may be part of and connected to one or more of the power distribution board 421 and the power storage device 400.

In the illustrated embodiment, the power storage device 420 is a battery. The battery 420 is mounted to a chassis of the external adjustment device 400, adjacent to a surface of the external adjustment device 400 enabling connection of a power supply to the external adjustment device 400 at a power supply input 422. The battery 420 includes a power interface board 421, configured to interface with and communicate power to the motor 430. The power interface board 421 may be operably coupled to one or more of the motor 430 and the control interface board 411. The power interface board 421 may also communicate electrical energy from one or more of a power supply input 422 and the power storage device 420, to the controller 410.

The actuator of the external adjustment device 400 includes an electronic motor 430. The driver of the external adjustment device 400 includes a magnet 440 rotatably coupled to the electronic motor 430. The motor 430 may be operably connected to one or more of the controller 410, the control interface board 411, the power interface board 421 and the internal power storage device 420. In the illustrated embodiment the electronic motor 430 is operably connected to the internal power storage device 420 by the power interface board 421. The power interface board 421 may include power distribution circuits to communicate electrical energy to the electronic motor 430 from one or more of the power supply input 422 and the internal power storage device 420. The power interface board 421 may also be operably connected to the control interface board 411, to relay control information from the controller 410 to the motor 430. In some embodiments, the controller 410 may be in direct communication with the motor 430, and in some embodiments the controller 410 may be connected to the electronic motor via a wireless connection, for example a Bluetooth® connection.

The motor 430 may include any type of motor capable of rotating the magnet 440. The motor 430 is an electric motor and may include a rotational speed sensor 432. The rotational speed sensor 432 connected to and in communication with one or more of the control interface board 411 and the controller 410. In some embodiments, the internal speed sensor 432 may include for example one or more of an encoder and a digital output of an electronic motor. In some embodiments, the motor 430 is configured to communicate rotational speed data to the controller 410 wirelessly.

Figure 10:
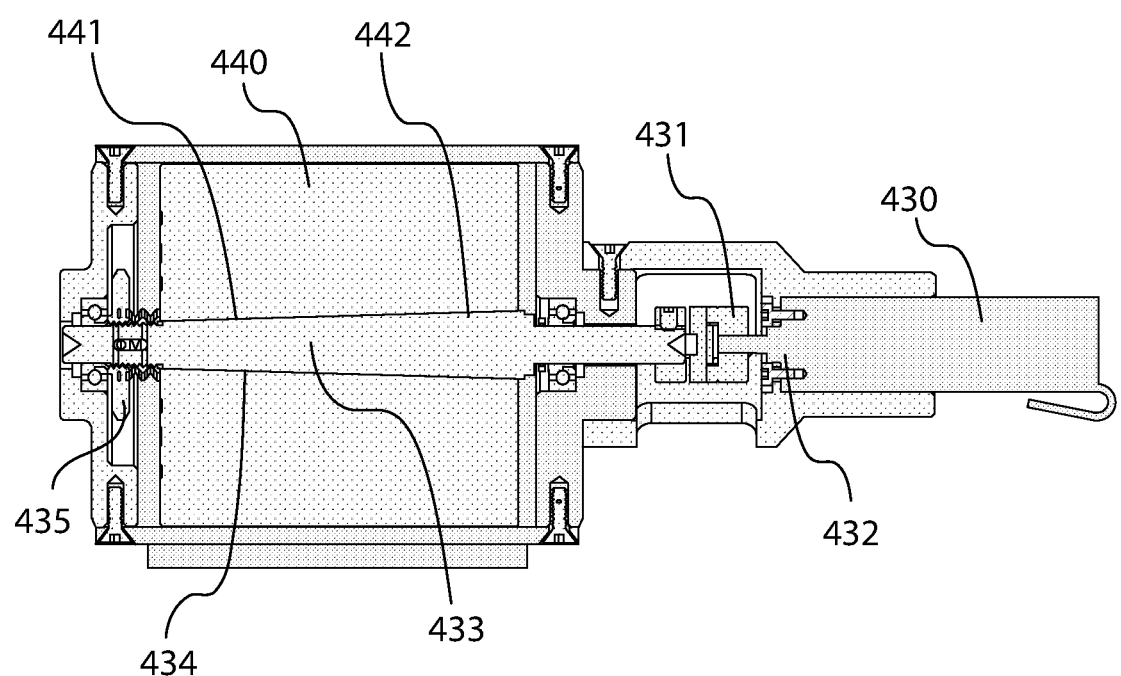
FIG. 10 shows a cross-sectional view of a magnet drive system including a motor having an internal motor speed sensor.

FIG. 10 shows an enhanced cross-sectional view of the motor 430 and the magnet 440 of the external adjustment device 400 in accordance with a first embodiment. The magnet 440 is shown rotatably coupled to the motor 430 by one or more couplings 431. In the illustrated embodiment, the magnet 440 includes an internal cavity 441 having an internal surface 442 and having a tapered profile. A magnet drive shaft 433 is shown including a magnet contact surface 434 having a tapered profile. The tapered profile of the magnet drive shaft 433 is configured to communicate with the tapered profile of the internal surface 442 of the magnet 440. This enables the magnet 440 to be secured to the magnet drive shaft 433 by a friction fit, the magnet 440 configured to be held onto the magnet drive shaft 433 by a cap 435 and the communicating tapered profiles. In some embodiments, the magnet 440 may be attached to the magnet drive shaft 433 using an adhesive material.

The magnet 440 may comprise any magnetic element including a radially polarized cylindrical magnet, a permanent magnet, an electro magnet, and any other magnetic element known and used in the art. The magnet 440 is configured to magnetically couple with a permanent magnet 262 of an adjustable implant and to rotate the permanent magnet 262 and adjust the adjustable implant 200. Upon a rotation of the magnet 440, a rotating magnetic field will be generated, placing a force on the magnetically coupled permanent magnet 262 of the adjustable implant 200, thereby inducing a rotation of the permanent magnet 262 and subsequent adjustment of the adjustable implant 200.

In some embodiments, the external adjustment device 400 includes one or more sensors configured to monitor a rotational speed of the magnet 440. In some embodiments, the sensors include magnetic sensors, for example Hall-Effect sensors disposed on one or more of the housing 401, a plate, and a chassis, and may be placed adjacent to the magnet 440. In some embodiments, the sensors include photo-sensors. The magnet may include one or more circular optical encoder strips to work in conjunction with the photo-sensors. U.S. patent application Ser. No. 14/932,904 describes various systems and methods for non-invasively detecting the force generated by a non-invasively adjustable implant, the entire contents of which are hereby incorporated by reference.

In the illustrated embodiment the external adjustment device 400 includes a motor 430 having one or more rotational speed sensor 432 configured to detect a change in a motor angular velocity (V), and thereby as described below non-invasively detect a rotation of the permanent magnet 262 of the adjustable implant 200. The motor 430 has torque characteristics that allows for little variation in motor angular velocity (V) during a motor rotation and corresponding magnet 440 rotation, when there is no implant or ferrous material located near the ERC magnet or magnetically coupled to the magnet 440.

When an adjustable implant 200 having a permanent magnet 262 is in close proximity to the rotating magnet 440, and for example magnetically coupled to the magnet 440, the magnetic poles of both magnets causes a changing load on the motor 430 twice per revolution. This causes the magnet 440 to increase or decrease in angular velocity, with the variations detectable by the rotational speed sensor 432.

Figure 11A:
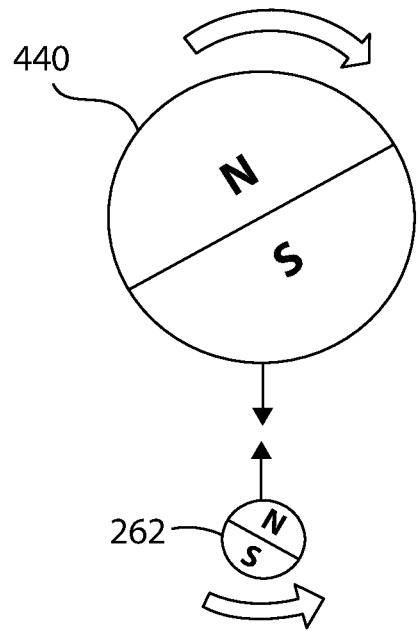
FIG. 11A shows a magnet of an external adjustment device magnetically coupled to a permanent magnet of an adjustable implant.
Figure 11B:
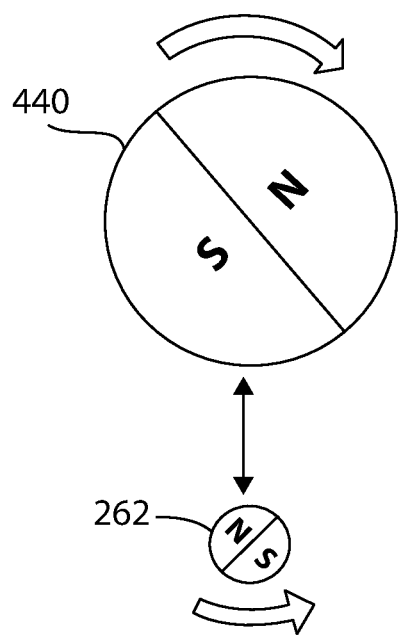
FIG. 11B shows a magnet of the external adjustment device magnetically coupled to the permanent magnet of the adjustable implant.

In FIG. 11A the magnet 440 of the external adjustment device 400 is shown rotating in a first clockwise direction, with the permanent magnet 262 of the implant shown magnetically coupled to the magnet 440 and rotating in a second counter clockwise direction. As one with skill in the art may appreciate, as the motor 430 drives rotation of the magnet 440 the respective poles of the magnet 440 and the permanent magnet 262 will attract each other, placing a reduced load on the motor 430 to drive the rotation as the poles are directed towards each other. Comparatively in FIG. 11B, as the motor 430 continues to drive rotation of the magnet 440 the respective poles of the magnet 440 and the permanent magnet M will still attract each other, placing an increased load on the motor 430 to drive the rotation as the poles are directed away from each other. These changes in load result in observable changes of the angular velocity that can be detected by the rotational speed sensor 432 of the motor 430.

The rotational speed sensor 432 measures the angular velocity of motor 430 which corresponds to an angular velocity of the magnet 440, and communicates the angular velocity to the controller 410. In some embodiments, the angular velocity may be detected by quadrature encoder signals obtained from the motor 430. The encoder provides an electronic pulse or signal that represents a "tick" for a step in the revolution of the magnet 440. In this embodiment, there may be for example, the encoder sends 90 "ticks" per revolution of the magnet 440 or one for each of the 4 degrees of the full 360 degrees of rotation. The number of "ticks" used per rotation can be any number chosen, and may depend on an amount of resolution desired for a given measurement. One or more of the controller 410 and a control interface board 411 may provide control circuits to the motor 430 as well as detection circuits of the encoder signals, and may include the internal speed sensor 432.

Figure 12:
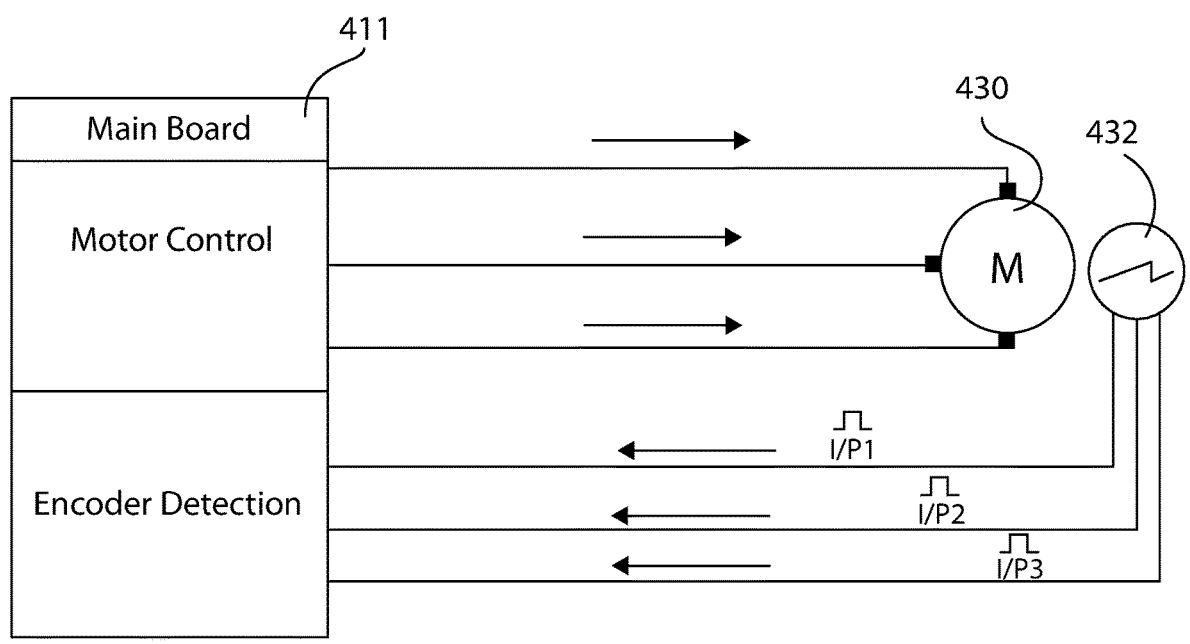
FIG. 12 shows a schematic of motor control and encoder detection signal communication.

FIG. 12 shows a diagram of the motor 430 control signals and encoder 413 detection signals for angular velocity and remote magnet rotation detection. The main board, which may include the control interface board 411, may communicate instructions to the motor 430. The encoder 432 may return pulses representing "ticks" for a step in the revolution of the magnet 440. Using the returned encoder signals representing a "tick" every n degrees, the angular velocity may be calculated in rpms using the equation below:

$$V = \frac{t}{T_t \times R_t}$$

Where: t equals seconds in one minute (60 seconds/min), $R_t$ equals the number of ticks per revolution (which in this embodiment would be 90 ticks/revolution), and $T_t$ is the observed the time between ticks in seconds. Using this equation, a calculated angular velocity can be obtained using the time difference between ticks for every tick detected.

Figure 13:
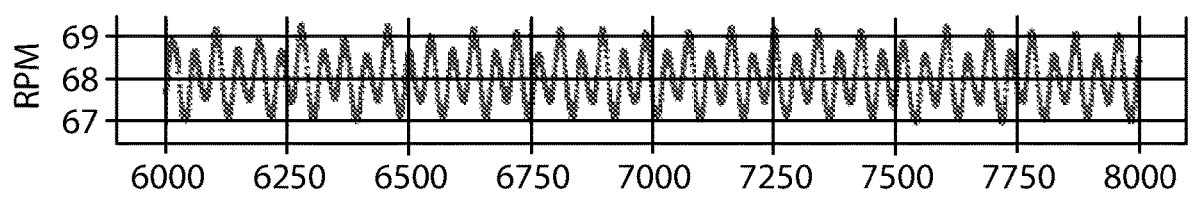
FIG. 13 shows a plot of rotational speed of the motor and shows the two maximum values and two minimum values of the angular velocity (RPM) observed by the motor.

FIG. 13 shows a measured graph of the angular velocity of the magnet 440 for one revolution with the magnet 440 coupled to a permanent magnet 262. Note that there are two observed maximum peaks and two observed minimum peaks which correspond with the changes in loads along the magnetic poles during the magnet revolution, as was discussed above.

A binary observation of whether or not the magnet 440 of the external adjustment device 400 is magnetically coupled to the magnet 262 of the adjustable implant 200 can be obtained by monitoring how tightly bound the rotational speed or angular velocity of the motor 430 is to an average value.

Figure 14A:
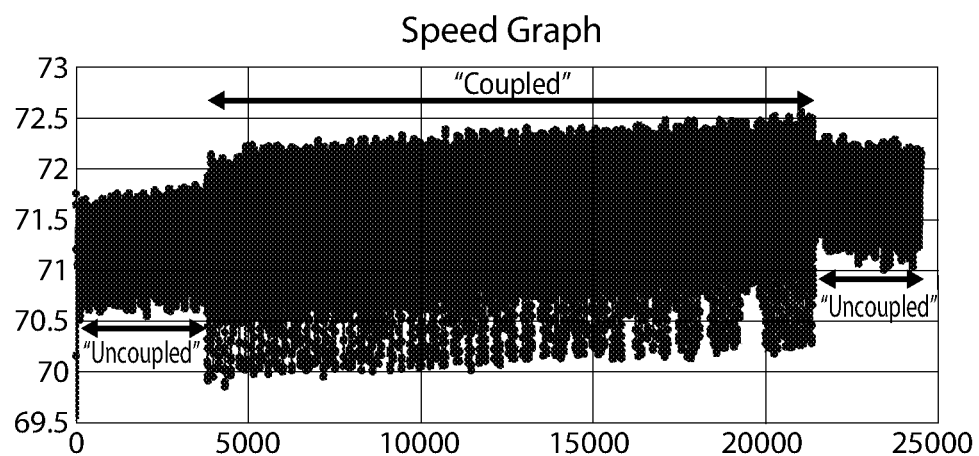
FIG. 14A shows a graph tracking a rotational speed of the motor vs time.

FIG. 14A shows a graph measuring a rotational speed of the motor 430 plotted over time as the magnet 440 is coupled to and adjusts a permanent magnet 262 of an adjustable implant 200.

First, in a magnetically uncoupled state, the speed of the motor 430 remains tightly bound to an average value. In a magnetically uncoupled state, the magnet 440 of the external adjustment device 400 is free to rotate in response to the torque supplied by the motor 430, and is free of any added influence from a coupled permanent magnet 262 of an adjustable implant 200.

In a magnetically coupled state, larger fluctuations are observed in the speed of the motor 430, as a result of the added influence from a coupled permanent magnet 262 of an adjustable implant 200.

Figure 14B:
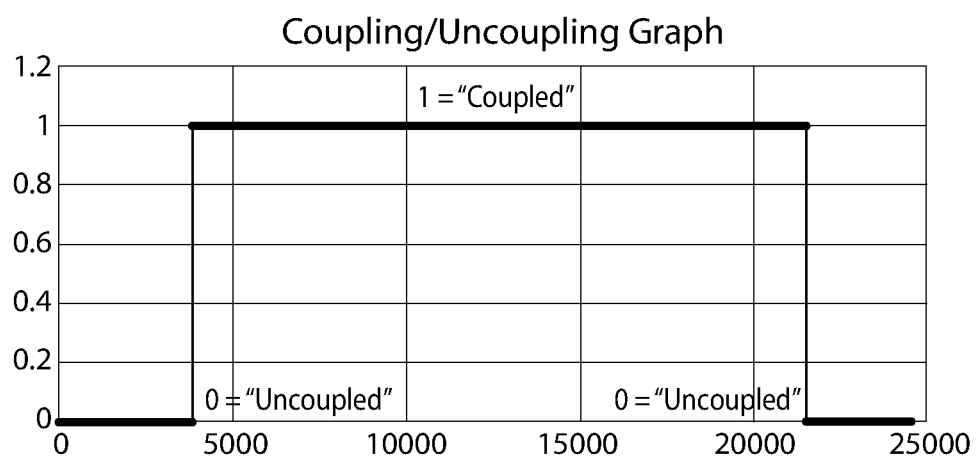
FIG. 14B shows a graph tracking a coupled state of the magnet vs time.

Therefore, by measuring a rotational speed of the magnet 440 of the external adjustment device 400 one can determine whether the magnet 440 is in a magnetically coupled or uncoupled state with a permanent magnet 262 of an adjustable implant as shown in FIG. 14B. This determination can be communicated to the controller 410, and subsequently displayed to a user, non-invasively providing the user with reassurance that the magnet 440 is coupled to the permanent magnet 262 of the adjustable implant 200 during treatment.

By measuring the rotational speed of the magnet 440, one can detect one or more of: a magnetic coupling state; stalling of the permanent magnet 262; a relative GAP estimation; and a relative force estimation.

GAP is a distance from the magnet 440 of the external adjustment device 400 to a permanent magnet 262 of an adjustable implant 200. GAP can be estimated by measuring the rotational speed of the magnet 440 of the external adjustment device 400 in a magnetically coupled state with a permanent magnet 262 of an adjustable implant 200. A GAP reference for a particular unit may be calibrated initially, for example during manufacturing. To obtain the reference, the rotational speed of the magnet may be measured at a known GAP distance. The Amplitude of the rotational speed waveform will change in response to and proportionally relative to a change in distance (GAP) between the magnet 440 and the permanent magnet 262. The observed amplitude of the speed graph will change proportional to the relative distance, allowing the controller 410 to estimate a GAP distance.

Force applied by the adjustable implant can also be estimated by observing the rotational speed of the at least one magnet 440 of the external adjustment device 400 over time. By measuring the rotational speed of the at least one the magnet 440 and simultaneously estimating the GAP, an estimation of the force being applied to the permanent magnet 262 of the adjustable implant 200 can be estimated.

In some embodiments, the adjustable implant 200 may have one or more planetary gear sets configured to change an amount of force delivered by the permanent magnet 262 of the adjustable implant 200. Characteristic properties may be programmed into one or more of the external adjustment device 400 and the controller 410, or may be communicated thereto by the adjustable implant 200. As one with skill in the art may appreciate, this communication may be achieved using, for example, an RFID tag of the adjustable implant, radiofrequency communication, ultrasonic communication, a Wi-Fi connection and any other type of communication known in the art.

Stalling is a failure of a permanent magnet 262 of an adjustable implant 200 to rotate in response to the rotation of the magnet 440 of the external adjustment device 400. In order to detect a stall condition of the permanent magnet 262 of the adjustable implant 200, a higher resolution of measurement of the angular velocity of the magnet 440 is required.

In some embodiments, this may be achieved by calculating the acceleration (ΔV) of the magnet. For example, subtracting the angular velocity of a final tick from the angular velocity of an initial tick, instantaneous acceleration may be determined for the current tick. This subtraction process may occur throughout the entire revolution of the magnet 440. The acceleration ΔV may vary since the magnet velocity slope may vary. This provides two maximum peaks as well as two minimum peaks associated with the changing velocity during the revolution. When the angular velocity of the magnet 440 is at a maximum or minimum peak, the acceleration will be zero (at axis) since the velocity slope is zero.

With the higher resolution of sensing to monitor acceleration, there are variables within the external adjustment device 400 that may cause the acceleration of the magnet 440 to vary even if no implant is in close vicinity of the magnet 440.

Figure 15A:
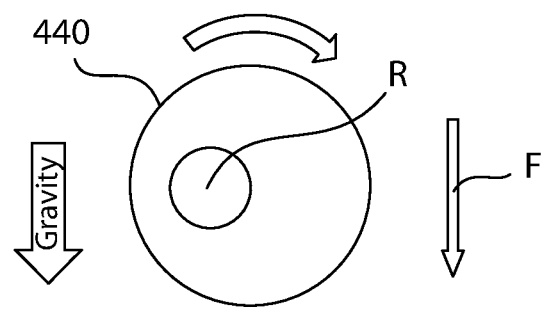
FIG. 15A shows a magnet of an external adjustment device, being driven to rotate in a clockwise direction having a non-concentric axis of rotation.
Figure 15B:
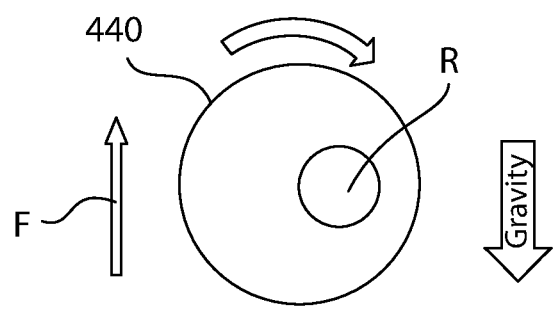
FIG. 15B shows a magnet of an external adjustment device, being driven to rotate in a clockwise direction having a non-concentric axis of rotation.

For example, when the external adjustment device 400 is uncoupled from the permanent magnet 262 of the adjustable implant, extraneous forces may be caused by a lack of concentricity in the rotation of the magnet 440 relative to its rotational axis R as illustrated in FIG. 15A and FIG. 15B.

FIG. 15A shows a magnet 440 of an external adjustment device 400, being driven to rotate in a clockwise direction as indicated. As one with skill in the art may appreciate, the magnet 440 is configured to rotate around a first axis R. Note that the first axis R is not concentric with the center of mass of the magnet 440. As such, with each rotation, gravity will add increased forces to each rotation, which may appear similar to a coupled permanent magnet 262, with these changes in load resulting in observable changes of velocity and acceleration that can be detected by the internal speed sensor 432 of the motor 430.

In FIG. 15A as the motor 430 continues to drive rotation of the magnet 440, the nonconcentric axis of rotation will result in a large torque being observed from gravitational forces, placing first a decreased load on the motor 430 to drive the rotation. As shown in FIG. 15B, after the magnet 440 reaches the bottom of its full rotation, the motor 430 will see an increased load due to an increased load on the motor 430 to continue to drive the rotation.

Other variables may cause the magnet to accelerate and decelerate during its rotation include: points of friction within the axis, points of friction within the motor mechanism, the external adjustment device having two or more magnets with two or more magnetic poles attracting and repelling each other during rotation, other ferrous metal located inside and adjacent to the external adjustment device 400.

Figure 16A:
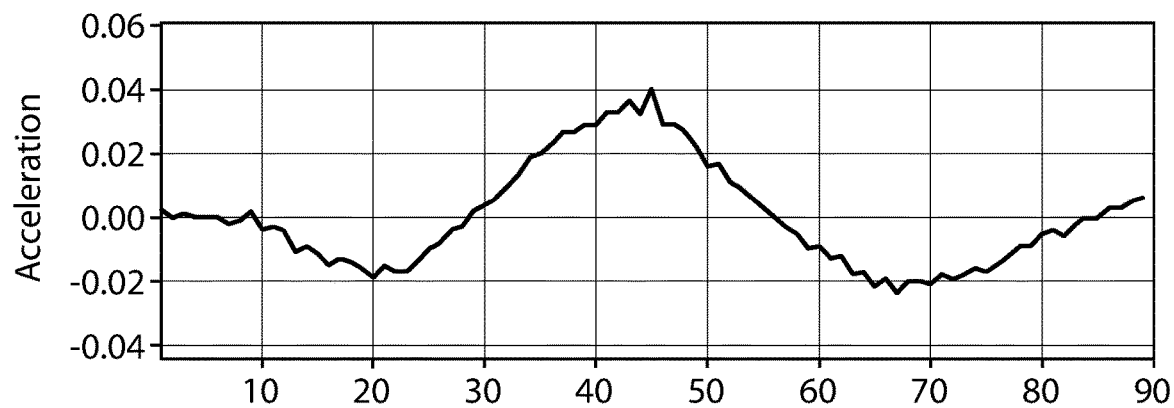
FIG. 16A shows a plot of acceleration plotted tick to tick for a single rotation of a magnet of an external adjustment device.
Figure 16B:
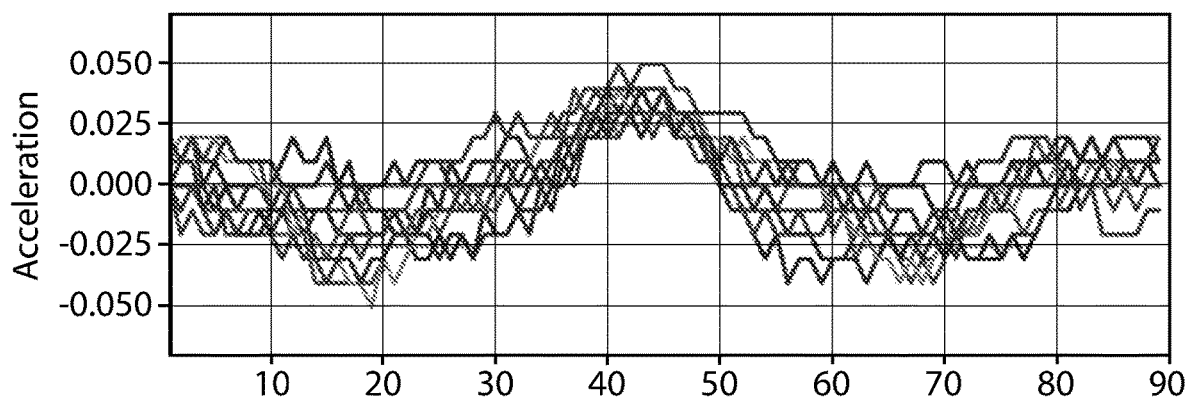
FIG. 16B shows plots of multiple rotations of the magnet and illustrates the variability within the external adjustment device from rotation to rotation.

FIG. 16A shows a plot of acceleration taken tick to tick for a single rotation of a magnet 440 of an external adjustment device 400. FIG. 16B shows plots of multiple rotations of the magnet 440 and illustrates the variability within the external adjustment device from rotation to rotation. Note the variations in amplitudes of acceleration and may even result in phase shifts.

The acceleration/deceleration profile and characteristics may be unique for each external adjustment device from unit to unit. Reasons for this may include methods of manufacturing and individual conformance to the concentricity variation from magnet to magnet and other factors as mentioned above.

For example, a perfectly concentric magnet, a frictionless drive mechanism, along with no ferrous metals inside and around the external adjustment device during operation may provide an ideal acceleration/deceleration profile of constant zero throughout a driven revolution of the magnet 440. Thus, any change in acceleration/deceleration detected would be associated with a permanent magnet 262 of an adjustable implant 200 allowing for improved detection performance needed for stall detection as well as a deep sensing range (measurement across large GAPs).

A method to mitigate the unwanted acceleration/deceleration characteristics inherent of the external adjustment device 400 is provided and includes the steps: ensuring the magnet 440 is uncoupled from a permanent magnet of an implant, obtaining a characterization profile by recording an acceleration/deceleration profile while the external adjustment device magnets are rotating. Once the unique characterization profile of the external adjustment device is determined, it may then be saved to memory.

Since the characterization profile waveform varies from the external adjustment device to device and rotation to rotation. Several profile samples may be captured into a 90 element array for each rotation. The characterization profile array is created by averaging each element in all rotational profile arrays captured. Before averaging, the acceleration peak for each rotational array is detected. Each detected acceleration peak from each rotational array is shifted to the center (element 45). This filters any phase shifting. The average of each element for all arrays is determined and the characterization profile for the external adjustment device 400 is stored.

Figure 17:
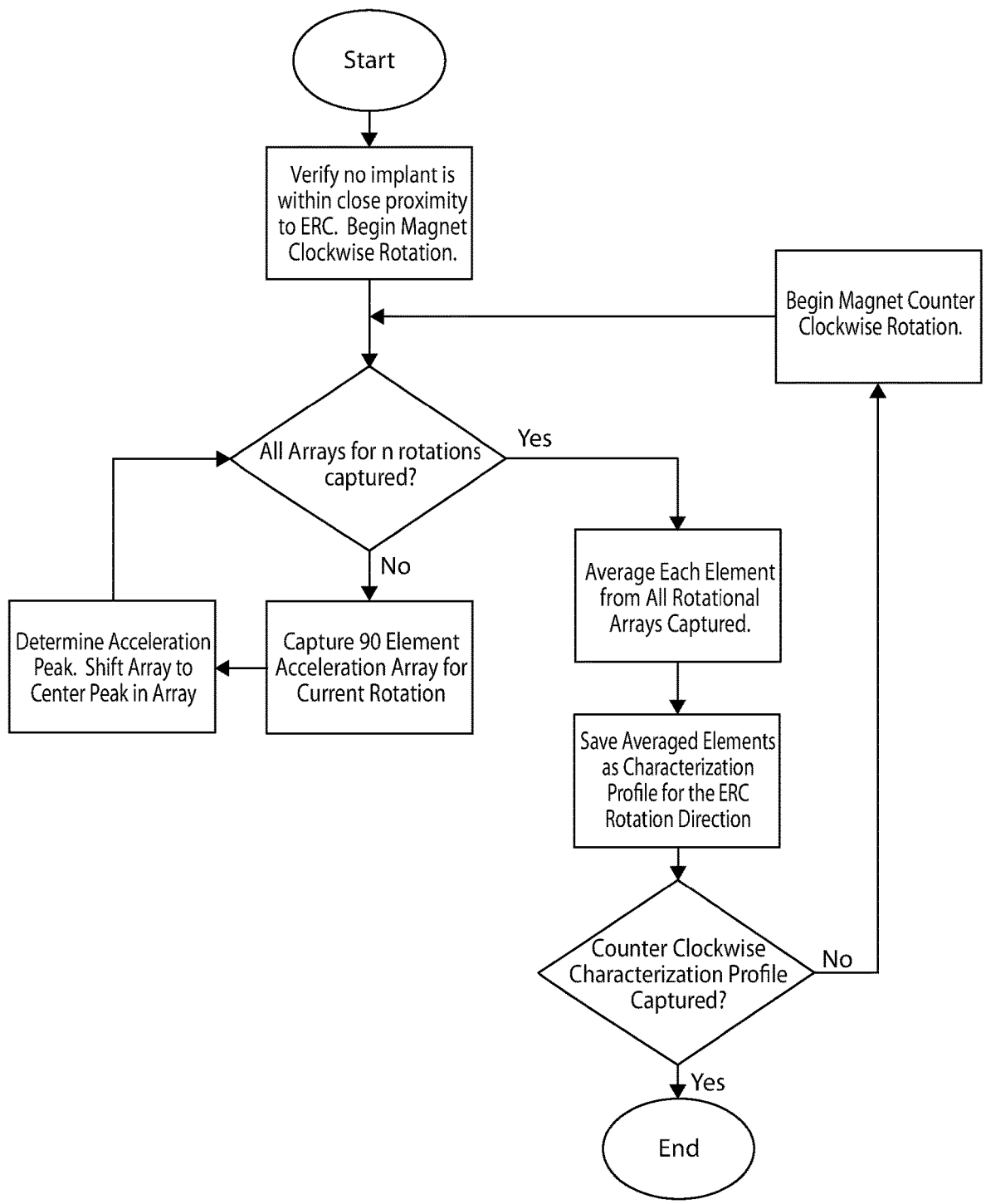
FIG. 17 shows a flow chart for a method for obtaining a characterization profile of an external adjustment device.

FIG. 17 shows an exemplary flow chart of method for obtaining a characterization profile of the external adjustment device 400, the method including the steps: Verifying no implants and ferrous materials in proximity to the external adjustment device 400, Rotating a magnet 440 of the external adjustment device 400, Measuring an acceleration array during a rotation of the magnet 440, Determining an acceleration peak of the acceleration array, Shifting the acceleration array to the center peak, Averaging all acceleration arrays captured, and Saving averaged array as a characterization profile of the external adjustment device 400. In some embodiments, a counter clockwise characterization profile is obtained. In some embodiments, a clockwise characterization rotation profile is obtained. In some embodiments, both profiles can be obtained and may be averaged together.

The external adjustment device 400 uses the saved characterization profile as a reference to filter inherit and possibly undesired magnet acceleration/deceleration observed during use. While the magnet 440 of the external adjustment device 400 is rotating, an array is captured for a predetermined number of rotations. Similar to the steps to obtain the characterization profile, each array acceleration peak element is detected and shifted to the center of the array. An average of each element in the predetermined number of rotational arrays is averaged and an Averaged Rotation Array Waveform is captured and saved.

The Averaged Rotational Array Waveform may then be compared to the Characterization Profile. By subtracting the characterization profile from the averaged rotational array, we can obtain a test array.

If the external adjustment device 400 is uncoupled with no implant in proximity to the magnet 440 of the external adjustment device 400, the Averaged Rotational Array Waveform will look similar to the Characterization Profile. Subtraction of these arrays will bring the test array close to zero for all elements. The test array is reviewed for peak amplitude, which is small, and compared to a predetermined threshold. If the test array waveform peak to peak amplitude is below a threshold, the external adjustment device 400 has detected an uncoupled condition during its use.

If the magnet 440 of the external adjustment device 400 is coupled with a permanent magnet 262 of an adjustable implant 200 in close proximity to the magnet 440, measurable acceleration and deceleration will be observed in the arrays captured. The waveform amplitude of the coupled arrays captured are significantly larger than uncoupled arrays due to the greater acceleration/deceleration of the magnet 440 caused by the close proximity of the permanent magnet 262 similar to as discussed above. These higher amplitude acceleration/deceleration arrays may be averaged and subtracted from the lower amplitude characterization profile. The subtraction of these two arrays still produces a high amplitude test array. This test array is compared to the same predetermined threshold used to detect uncoupled condition. If the test array waveform peak to peak amplitude is higher than the threshold, the external adjustment device 400 has detected a coupled condition during its use.

Figure 18:
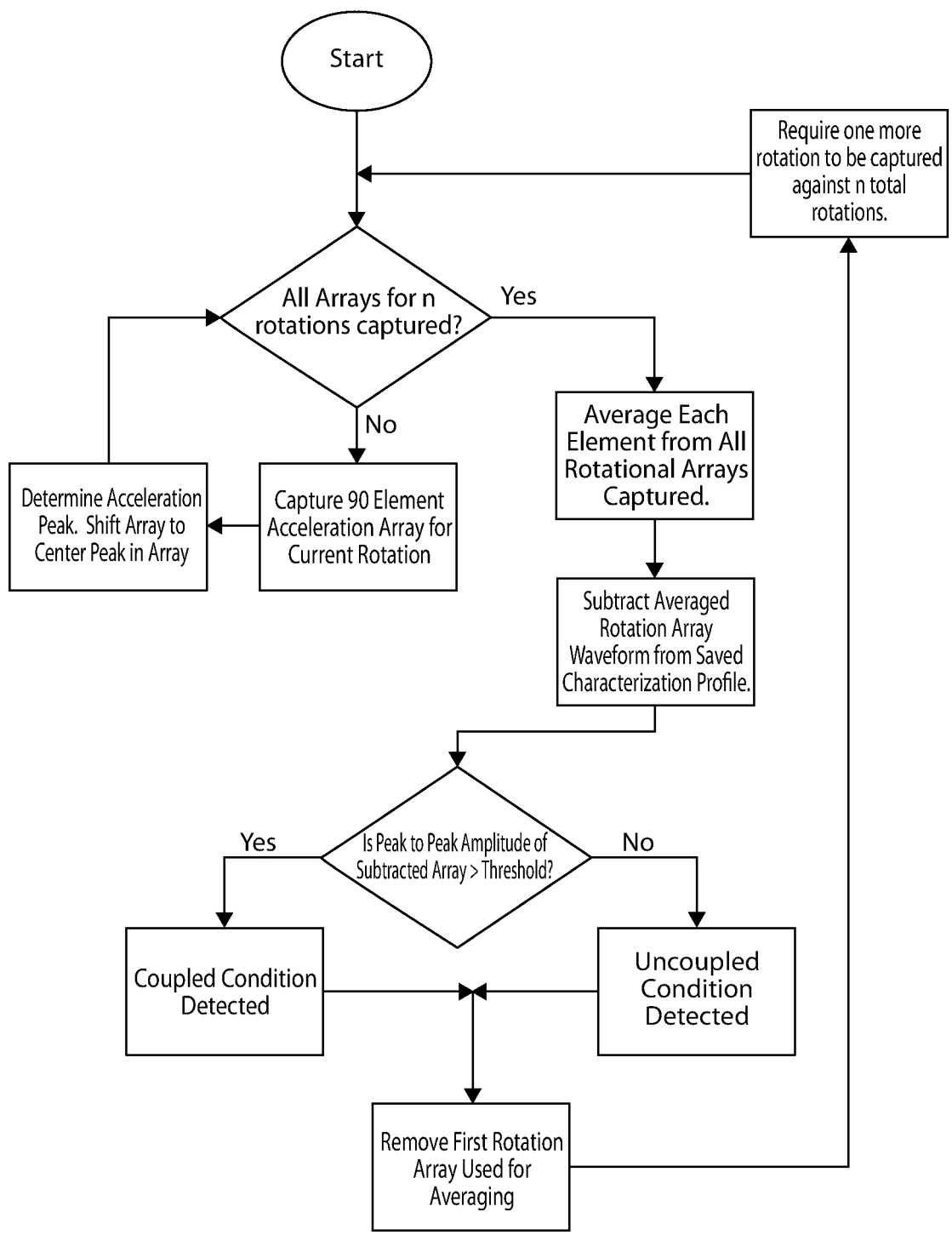
FIG. 18 shows a flow chart for a method of coupled state determination of a magnet of an external adjustment device with a permanent magnet of an adjustable implant.

FIG. 18 shows an exemplary flow chart of a method of coupled state determination of a magnet 440 of an external adjustment device 400 with a permanent magnet 262 of an adjustable implant 200, including the steps: rotating a magnet of the external adjustment device; measuring an acceleration array during a revolution of the magnet; determining an acceleration peak of the acceleration array; shifting the acceleration array to a center peak; averaging all acceleration arrays captured; subtracting averaged array from a characterization profile of the external adjustment device to obtain a test array; and comparing peak to peak amplitude of the test array to a threshold, wherein if peak to peak amplitude of the test array is greater than the threshold, then a coupled state is determined; and wherein if peak to peak amplitude of the test array is less than the threshold, then an uncoupled state is determined.

In some embodiments, the detected state may be communicated to the controller 410. In some embodiments, the detected state may be displayed to a user by the display 403. In some embodiments, the detected state may be communicated to the motor 430. In some embodiments, the detected state may be communicated to a tertiary device.

Detecting Stalling requires a higher resolution of detection of the angular velocity of the magnet 440 of the external adjustment device 400. This can be achieved by calculating the acceleration ($\Delta V$) of the magnet 440. By subtracting the angular velocity of the current detected tick from the previous velocity of the previous detected tick ($\Delta V$), an instantaneous acceleration can be determined for the current tick. This subtraction process occurs throughout the entire revolution, for example all 90 ticks corresponding to all 360 degrees of rotation. The $\Delta V$ does vary since the velocity slope of the magnet 440 of the external adjustment device 400 does vary. This provides two maximum peaks as well as two minimum peaks associated with the changing velocity in the revolution. When the angular velocity of the magnet 440 is at a maximum or minimum peak, the acceleration will be zero (at axis) since the velocity slope is zero.

Figure 19A:
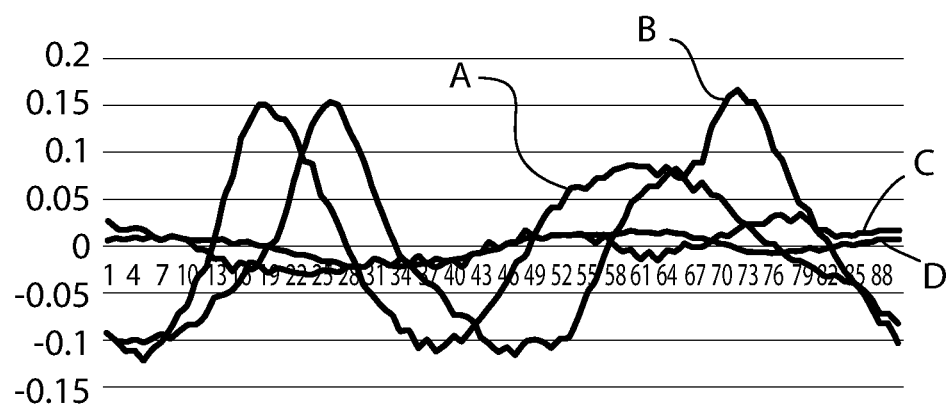
FIG. 19A shows a plot of the acceleration observed by the magnet during 360 degrees of rotation plotted as 90 ticks.

FIG. 19A shows waveforms of the acceleration observed by the magnet 440 during 360 degrees of rotation. The 360 degrees of rotation are broken down into 90 ticks, with the instantaneous acceleration ($\Delta V$) observed at each tick. This plot includes four arrays including a stalled rotation A, a coupled rotation B, an uncoupled rotation C, and an uncoupled average D.

Figure 19B:
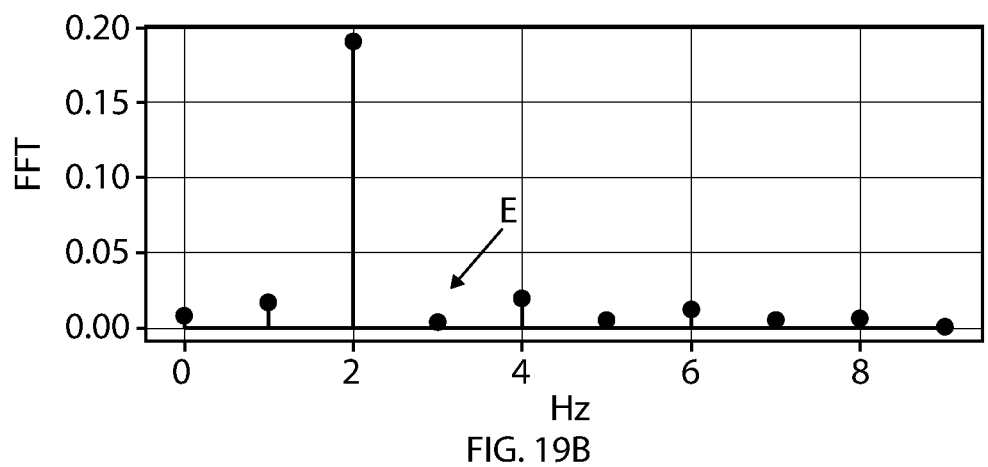
FIG. 19B shows a fast Fourier transform (FFT) analysis transforming the coupled waveform into the frequency domain to discriminate between a coupled state and a stall condition.
Figure 19C:
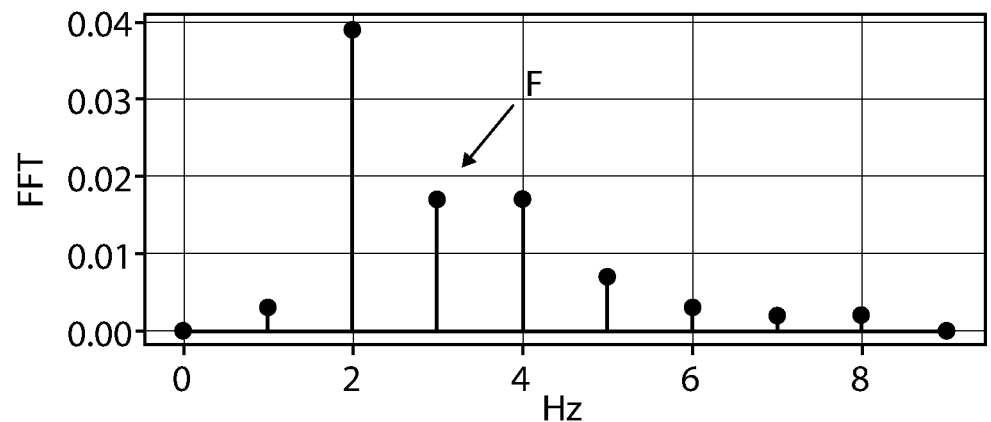
FIG. 19C shows a fast Fourier transform (FFT) analysis transforming the stalled waveform into the frequency domain to discriminate between the coupled state and the stall condition.

In some embodiments, the external adjustment device may analyze a third harmonic of a fast Fourier transform (FFT) of the acceleration array to determine the stalled condition. In FIG. 19B a fast Fourier transform (FFT) is shown transferring the coupled rotation B array into the frequency domain to discriminate between a coupled state and a stall condition by analyzing the third harmonic. In FIG. 19C a fast Fourier transform (FFT) is shown transferring the stalled rotation A array into the frequency domain to discriminate between the coupled state and the stall condition by analyzing the third harmonic. In comparison to FIG. 19B, notice that in the stalled condition a significant amplitude increase in the 3rd harmonic of the waveform's fast Fourier transform (FFT) is observed. The 3rd harmonic of the FFT is missing for the coupled condition E and is present for the stall condition F.

Stalling may cause large fluctuations in the amount of acceleration and the rotational speed of the magnet 440, due to high amounts of resistance placed on the rotation of the magnet of the external adjustment device 400, by the stalled permanent magnet 262 of the adjustable implant 200. Additionally, the rotation of the magnet 440 may be less concentric and less tightly bound to the average value as a result of added forces observed by the magnet 440 due to the magnetic field of the permanent magnet 262.

By taking a fast Fourier transform (FFT) and looking at the plot of angular velocity in the frequency domain, we can observe unwanted interference and false stalling signals. For example, if the magnet 440 is coupled to and rotating an internal permanent magnet 262 of an adjustable implant 200, and a foreign piece of ferrous metal is introduced and placed near the system, the system may be tricked into detecting a stall even though the internal permanent magnet 262 of the adjustable implant 200 is in fact rotating with the magnet 440. In the frequency domain, the foreign piece of metal will introduce an additional frequency signals to the FFT plot, which we can filter out and ignore. Preventing false stalling detection.

There are several dissimilarities between the fast Fourier transform (FFTs). However, this technique could be used to add other components to discriminate Stall as well discriminate outside ferrous metal in the vicinity of the magnet 440, which could disrupt the sensing performance for detection of the implant conditions.

In some embodiments, the external adjustment device 400 may discriminate a stall condition by analyzing the fast Fourier transform (FFT) and taking a ratio of the respective amplitudes of a first frequency component and a second frequency component. The threshold for detection is a value associated with the ratio. There are amplitude variations in the FFT that are caused by proximity of the permanent implant 262 to the magnet 440. In a coupled state, the observed ratio of a first frequency component and a second frequency component is above a threshold value. In a stalled state, the observed ratio of the first frequency component and a second frequency component is below a threshold value.

Figure 19D:
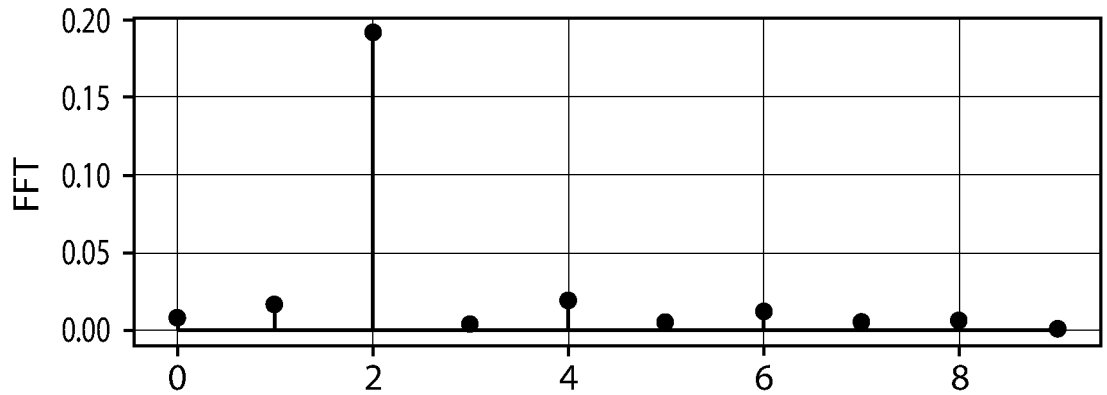
FIG. 19D shows a fast Fourier transform (FFT) analysis transforming a waveform corresponding to a strongly coupled condition into the frequency domain to discriminate between the coupled state and the stall condition.

For example, in FIG. 19D a fast Fourier transform (FFT) is shown which corresponds to a strongly coupled condition, for example where the magnet 440 is coupled to and rotating a permanent magnet 262 with a small GAP. Here we observe the 2nd harmonic at around 2 Hz which equal to 0.18 and divide it by the 4th harmonic at around 4 Hz which equals 0.025. Taking the ratio, we get a value of 7.2.

Figure 19E:
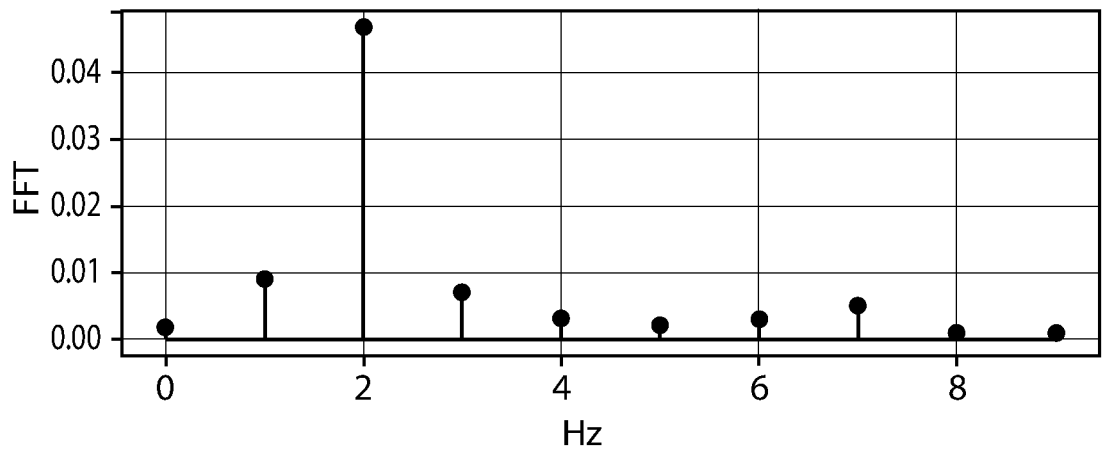
FIG. 19E shows a fast Fourier transform (FFT) analysis transforming a waveform corresponding to a weakly coupled condition into the frequency domain to discriminate between the coupled state and the stall condition.

In FIG. 19E a fast Fourier transform (FFT) is shown which corresponds to a weakly coupled condition, for example where the magnet 440 is coupled to and rotating a permanent magnet 262 with a large GAP. Here we observe the 2nd harmonic at around 2 Hz which equal to 0.48 and divide it by the 4th harmonic at around 4 Hz which equals 0.004. Taking the ratio, we get a value of 12.

Figure 19F:
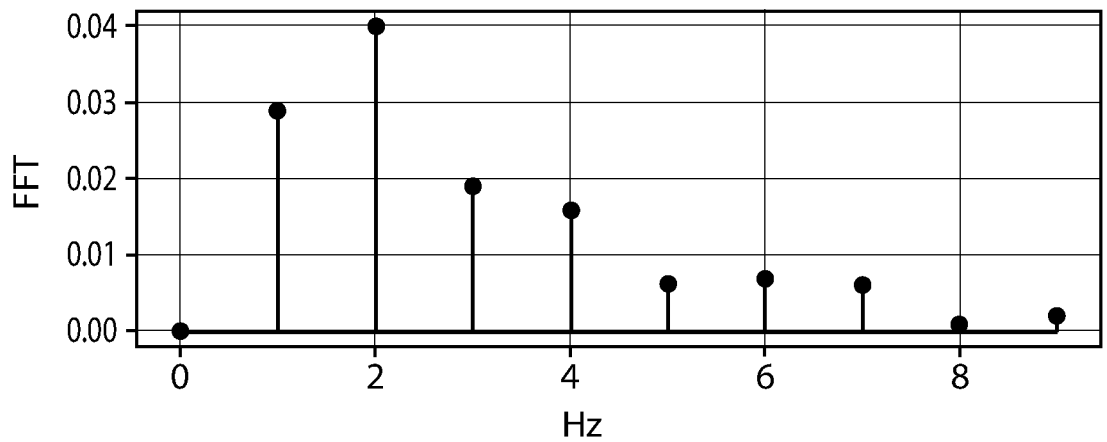
FIG. 19F shows a fast Fourier transform (FFT) analysis transforming a waveform corresponding to a stalled condition into the frequency domain to discriminate between the coupled state and the stall condition.

Now in FIG. 19F a fast Fourier transform (FFT) is shown which corresponds to a stalled condition, for example where the magnet 440 is not coupled to and not rotating a permanent magnet 262. Here we observe the 2nd harmonic at around 2 Hz which equal to 0.04 and divide it by the 4th harmonic at around 4 Hz which equals 0.016. Taking the ratio, we get a value of 2.5.

Therefore, threshold for ratio comparison has to be between 7.2 and 2.5 based on these graphs. Data has shown that for multiple implant configurations the threshold for ratio comparison is around 6.5, wherein a ratio value below 6.5 indicates a stall condition. Now as one with skill in the art may appreciate, these and other computations as shown and described herein may be obtained by one or more of the controller and the external adjustment device. The calculations may be performed during use with results and indications provided to a user. Additionally, the specific threshold may be unique from unit to unit.

Figure 20:
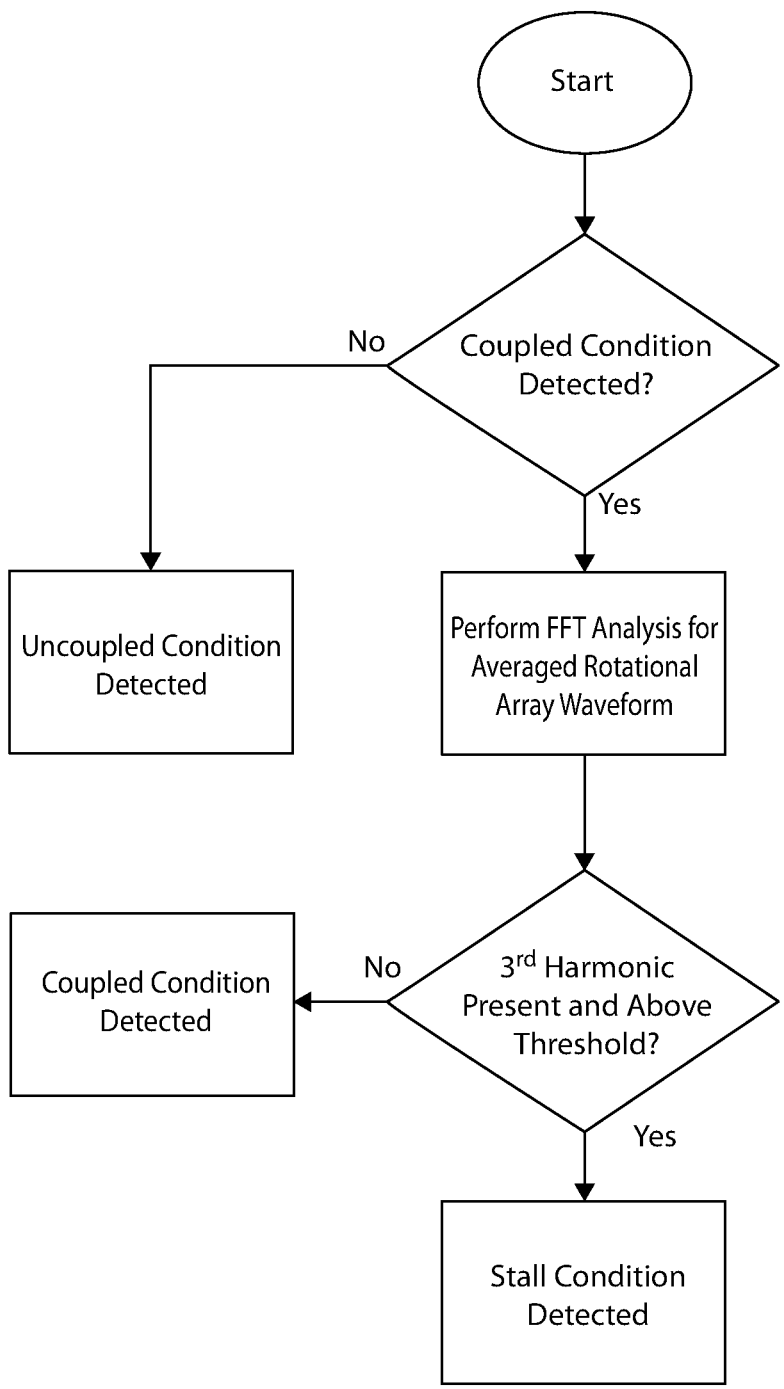
FIG. 20 shows a flow chart for a method of stalled state determination for a magnet of an external adjustment device and a permanent magnet of an adjustable implant.

FIG. 20 shows an exemplary flow chart of a method of stalled state determination for a magnet 440 of an external adjustment device 400 and a permanent magnet 262 of an adjustable implant 200, including the steps: rotating a magnet of the external adjustment device; measuring an acceleration array during a revolution of the magnet; determining an acceleration peak of the acceleration array; shifting the acceleration array to a center peak; averaging all acceleration arrays captured; subtracting averaged array from a characterization profile of the external adjustment device to obtain a test array; performing a fast Fourier transform (FFT) analysis for the test array; and observing 3rd harmonic, wherein if a 3rd harmonic is one or more of: present and above a threshold value, then a stalled state is determined, and wherein if a 3rd harmonic is one or more of: missing and below a threshold value, then no stalled state is detected and the magnets are coupled.

FIG. 21 A-D show an embodiment of a Graphical User Interface (GUI) for the external adjustment device 400. The GUI may be displayed on the display 403 of the external adjustment device 400. During operation of the external adjustment device 400, the GUI allows a user to input instructions to the external adjustment device 400, receive data from the external adjustment device 400, or otherwise operate the external adjustment device 400.

Figure 21A:
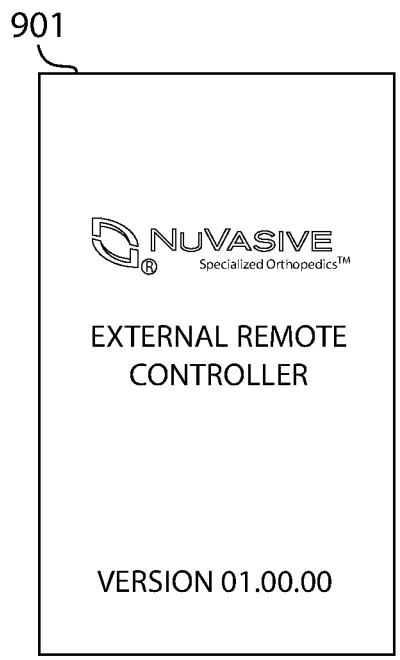
FIG. 21A shows a LOCK screen of a GUI in accordance with a first embodiment.

FIG. 21A shows a LOCK screen 901, which may be displayed when the external adjustment device 400 is inactive. In some embodiments, the external adjustment device 400 may be programmed to lock the device with the LOCK screen 901 displayed until the user enters a password. In some embodiments, the external adjustment device 400, is configured to remain locked until the external adjustment device 400 senses it is in proximity to an adjustable implant.

Figure 21B:
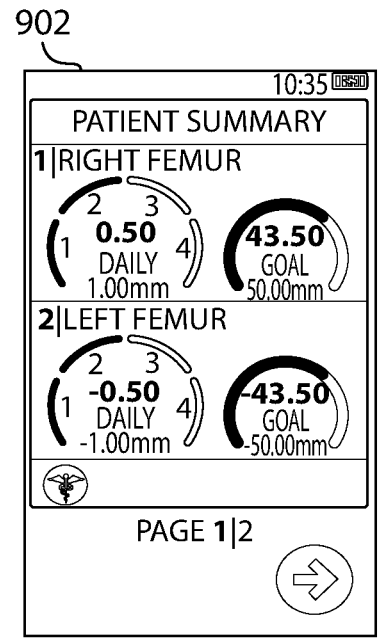
FIG. 21B shows a PATIENT SUMMARY screen of a GUI in accordance with a first embodiment.

FIG. 21B shows a PATIENT SUMMARY screen 902, which communicates individual patient adjustment information. The PATIENT SUMMARY screen 902 is shown displaying Daily distraction amount information, and total distraction goals for one or more long bone of a patient.

Figure 21C:
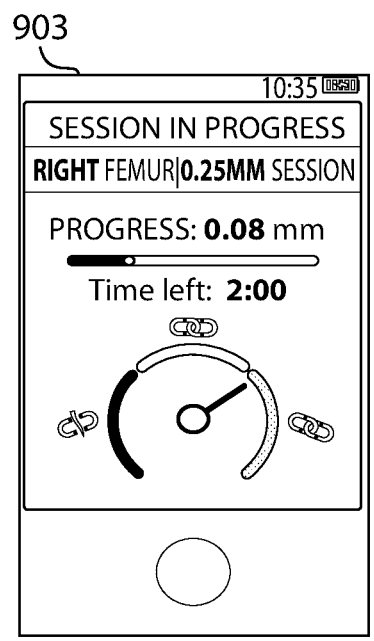
FIG. 21C shows a SESSION IN PROGRESS screen of a GUI in accordance with a first embodiment.

FIG. 21C shows a SESSION IN PROGRESS screen 903 which helps guide a user during operation of the external adjustment device. The SESSION IN PROGRESS screen communicates distraction information, and helps prevent over adjustment of the adjustable implant. The GUI may communicate one or more of a progress measurement, a session instruction, a coupled state indication, and a stalled state indication to a user.

Figure 21D:
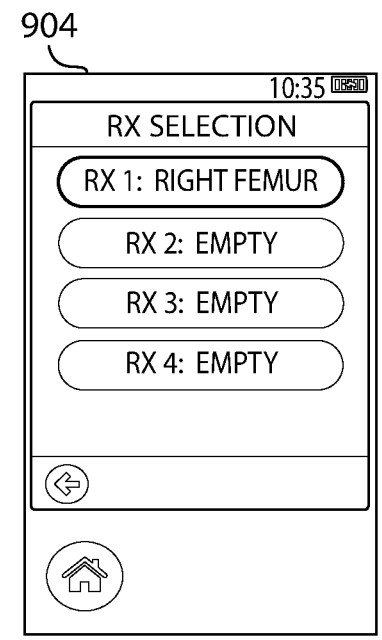
FIG. 21D shows a RX SELECTION screen of a GUI in accordance with a first embodiment.

FIG. 21D shows a RX SELECTION screen 904 which allows a user to select one of multiple treatment options. In some embodiments, the wireless communication components provide for cloud based data acquisition and storage. As discussed supra, the external adjustment device 400 may include wireless connection capabilities, for example, a wifi connection. A wifi connection and networking capabilities allow a second user to remotely access the external adjustment device to upload firmware, download adjustment data, upload treatment options, or remotely operate the device.

As one with skill in the art can appreciate, these exemplary embodiments of methods are not intended to be exhaustive. The blocks of the individual methods may be substituted and interchangeable between the various embodiments. Additional blocks may be added and substituted to the various embodiments corresponding to additional steps and features disclosed throughout these papers.

Now, although particular features and embodiments have been described in an effort to enable those with skill in the art to make and use the claimed invention, it should be understood that several variations, alterations or substitutions can be achieved to arrive at the subject matter disclosed. Nothing in this description shall be construed as limiting the spirit and scope of the invention as set forth in the appended claims, below.

What is claimed is:

1. An external adjustment device for non-invasively adjusting an implant, the external adjustment device comprising:
 a controller;
 a motor; and
 at least one magnet rotatably coupled to the motor;
 wherein upon placing the external adjustment device in proximity to an adjustable implant the at least one magnet is configured to magnetically couple with a permanent magnet of the adjustable implant;
 wherein upon a movement of the at least one magnet, the controller is configured to detect a magnetic coupling state of the at least one magnet with the permanent magnet of the adjustable implant; and
 wherein the controller is configured to determine an acceleration of the motor, and to use the acceleration to determine a stalling state of the at least one magnet with the permanent magnet of the adjustable implant.

2. The external adjustment device of claim 1, wherein the magnetic coupling state detected by the controller is one of a coupled state and an uncoupled state.

3. The external adjustment device of claim 1, wherein the controller is configured to determine a rotational speed of the motor.

4. The external adjustment device of claim 3, wherein the controller uses the rotational speed to determine the coupling state of the at least one magnet with the permanent magnet of the adjustable implant.

5. The external adjustment device of claim 1, wherein the determination is made by transforming an acceleration array using a fast Fourier transform (FFT).

6. The external adjustment device of claim 5, wherein the determination is made by observing a third harmonic of the fast Fourier transform (FFT).

7. The external adjustment device of claim 1, wherein the controller is configured to wirelessly communicate with and control the motor.

8. The external adjustment device of claim 1, the controller comprising a smartphone.

9. The external adjustment device of claim 1, further comprising a power storage device.

10. The external adjustment device of claim 9, wherein the power storage device is a battery.

11. The external adjustment device of claim 1, comprising a memory.

12. The external adjustment device of claim 1, comprising a display configured to communicate information to a user.

13. The external adjustment device of claim 12, wherein the information communicated to the user comprises a magnetic coupling state of the at least one magnet with the permanent magnet of the adjustable implant.

14. The external adjustment device of claim 12, wherein the information communicated to the user comprises an amount of change in at least one of: a dimension of the adjustable implant and a force on the adjustable implant.

15. The external adjustment device of claim 12, wherein the information communicated to the user comprises a speed of rotation of one or more of: the at least one magnet and the permanent magnet of the adjustable implant.

16. The external adjustment device of claim 1, wherein the controller is configured to prevent a change in a dimension of an implantable medical device beyond a pre-determined limit.

17. A system comprising the external adjustment device and the adjustable implant of claim 1.

18. An external adjustment device for non-invasively adjusting an implant, the external adjustment device comprising:
- a controller;
- a motor; and
- at least one magnet rotatably coupled to the motor;
- wherein upon placing the external adjustment device in proximity to an adjustable implant, the at least one magnet is configured to magnetically couple with a permanent magnet of the adjustable implant; and
- wherein the controller is configured to determine an acceleration of the motor, and to use the acceleration to determine a stalling state of the at least one magnet with the permanent magnet of the adjustable implant by transforming an acceleration array using a fast Fourier transform (FFT).

\* \* \* \* \*